(12) United States Patent
Radmall et al.

(10) Patent No.: US 10,568,718 B2
(45) Date of Patent: *Feb. 25, 2020

(54) FORCE MODULE FOR ORTHODONTIC CORRECTION

(71) Applicant: ULTRADENT PRODUCTS, INC., South Jordan, UT (US)

(72) Inventors: Colby M. Radmall, Lehi, UT (US); V. Timothy Wood, South Jordan, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/808,163

(22) Filed: Nov. 9, 2017

(65) Prior Publication Data

US 2018/0064511 A1    Mar. 8, 2018

Related U.S. Application Data

(63) Continuation of application No. 14/769,373, filed as application No. PCT/US2014/017797 on Feb. 21, 2014, now Pat. No. 9,867,681.

(Continued)

(51) Int. Cl.
*A61C 7/36* (2006.01)
*A61C 7/28* (2006.01)

(52) U.S. Cl.
CPC ............... *A61C 7/36* (2013.01); *A61C 7/282* (2013.01)

(58) Field of Classification Search
CPC ...................................................... A61C 7/36
See application file for complete search history.

(56) References Cited

U.S. PATENT DOCUMENTS

| 4,571,178 A | 2/1986 | Rosenberg |
| 5,562,445 A | 10/1996 | DeVincenzo et al. |

(Continued)

FOREIGN PATENT DOCUMENTS

| WO | WO9953858 | 10/1999 |
| WO | WO03105717 | 12/2003 |
| WO | WO2012018648 | 2/2012 |

OTHER PUBLICATIONS

Supplementary European Search Report issued in European Application No. EP14753631, dated Sep. 22, 2016.

(Continued)

*Primary Examiner* — Ralph A Lewis
(74) *Attorney, Agent, or Firm* — Workman Nydegger

(57) ABSTRACT

Force modules and assemblies for use in orthodontic corrections include an elongate hollow outer body extending between proximal and distal ends, a plunger, biasing member (e.g. spring), and push rod. The plunger and push rod are slidably received within different ends of the hollow outer body. The biasing member is positioned within the hollow outer body and provides an expansion force, which provides a desired corrective force. The outer body, plunger, biasing member, and push rod can be configured in a telescoping relationship in order for the components to be telescopically compressed and expanded during use. The distal end can include a bendable pin or latch mechanism for attachment to a buccal tube. The push rod can include a hook, hole, or slot for attachment to an archwire. Various connectors for coupling an orthodontic force module to a buccal tube portion of a molar bracket are also disclosed.

20 Claims, 36 Drawing Sheets

Related U.S. Application Data

(60) Provisional application No. 61/768,687, filed on Feb. 25, 2013.

(56) References Cited

U.S. PATENT DOCUMENTS

| | | | |
|---|---|---|---|
| 5,711,667 A * | 1/1998 | Vogt | A61C 7/36 433/19 |
| 5,738,514 A | 4/1998 | DeVincenzo et al. | |
| 5,829,975 A | 11/1998 | Gold | |
| 5,944,518 A | 8/1999 | Sabbagh | |
| 5,964,588 A | 10/1999 | Cleary | |
| 6,162,051 A | 12/2000 | Brehm et al. | |
| 6,322,357 B1 | 11/2001 | Vogt | |
| 6,669,474 B2 | 12/2003 | Vogt | |
| 6,719,557 B1 | 4/2004 | Williams | |
| 6,913,460 B2 | 7/2005 | Cleary | |
| 7,018,202 B2 | 3/2006 | Teramoto | |
| 7,578,672 B2 | 8/2009 | Sheikh et al. | |
| 7,785,102 B2 | 8/2010 | Papadopoulos | |
| 8,348,664 B2 | 1/2013 | Sheikh | |
| 8,371,846 B2 | 2/2013 | Kishi | |
| 9,867,681 B2 * | 1/2018 | Radmall | A61C 7/36 |
| 2002/0025502 A1 | 2/2002 | Williams | |
| 2009/0035715 A1 | 2/2009 | Cleary | |
| 2011/0300502 A1 | 12/2011 | Kishi | |
| 2012/0028208 A1 | 2/2012 | Cleary | |
| 2013/0177861 A1 | 7/2013 | Hayes | |
| 2014/0072928 A1 | 3/2014 | Morin | |

OTHER PUBLICATIONS

"Detent". Def. American Heritage Dictionary. $5^{th}$ ed. 2016.

* cited by examiner

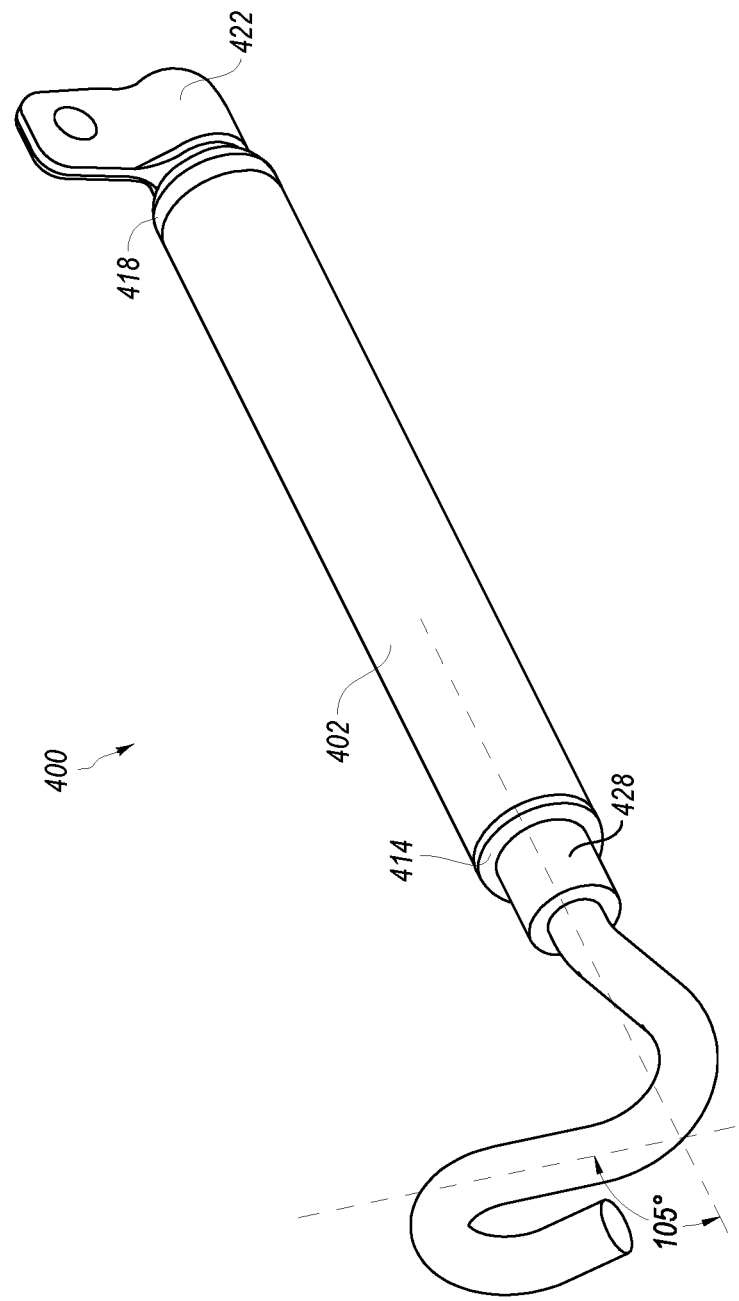

FORCE MODULE FOR ORTHODONTIC CORRECTION

CROSS REFERENCE TO RELATED APPLICATIONS

This application is a continuation of U.S. application Ser. No. 14/769,373, filed Aug. 30, 2015, which is a 371 application of International Patent Application No. PCT/US2014/017797, filed Feb. 21, 2014, which claims the benefit of U.S. Provisional Application No. 61/768,687, filed Feb. 25, 2013, the disclosures of which are incorporated herein in their entirety.

BACKGROUND OF THE INVENTION

1. The Field of the Invention

The present invention is in the field of orthodontics, more particularly in the field of devices for correction of class II and/or class III malocclusions.

2. The Relevant Technology

Orthodontics is a specialized field of dentistry that involves the application of mechanical forces to urge poorly positioned or crooked teeth into correct alignment and orientation. Orthodontic procedures can be used for cosmetic enhancement of teeth, as well as medically necessary movement of teeth to correct overjets and/or overbites. For example, orthodontic treatment can improve the patient's occlusion, or enhanced spatial matching, of corresponding upper and lower teeth.

The most common form of orthodontic treatment involves the use of orthodontic brackets and wires, which together are commonly referred to as "braces." Orthodontic brackets are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the bracket slots.

The brackets and the arch wire cooperate to guide corrective movement of the teeth into proper alignment. Typical corrective movements provided by orthodontic treatment can include lateral migration, torque, rotation, angulation, leveling, and other movements needed to correct the spacing and alignment of misaligned teeth.

The orthodontic treatment of some patients includes correction of the alignment of the upper dental arch relative to the lower dental arch. Certain patients have a condition referred to as a Class II malocclusion, which is a condition involving the posterior relationship of the mandible to the maxillae and in which the mesiobuccal cusp of the permanent maxillary first molar occludes mesial to the buccal groove of the permanent mandibular first molar (also known as retrognathia, or overjet). Other patients may have an opposite condition referred to as a Class III malocclusion wherein the lower dental arch is located forward of the upper dental arch when the jaws are closed (prognathia, or negative overjet).

Class II and Class III malocclusions may be corrected with the use of a force-applying system such as headgear, elastic, or an intraoral force module. Headgear is generally disfavored because it is bulky and often a source of embarrassment for the patient. Intraoral force modules have gained increasing acceptance as they can remain fixed in place over the course of treatment so as to typically not be removable by the patient, and are less aesthetically objectionable compared to traditional headgear.

Examples of intraoral force modules are disclosed in PCT Publication No. WO 2012/018648 and U.S. Pat. Nos. 5,828,875; 5,738,514; 5,711,667; 5,562,445; 6,358,046; 6,162,051; 5,964,588; and 5,944,518, the disclosures of which are incorporated herein by reference. Although existing intraoral force modules represent an improvement over headgear, they still have deficiencies that provide opportunities for substantial improvement.

SUMMARY OF THE INVENTION

Disclosed herein are orthodontic force module assemblies and force modules for use in correcting class II and/or class III malocclusions. Also disclosed herein are selectively lockable and unlockable attachment devices for attaching an orthodontic force module to an orthodontic bracket, such as a buccal tube and an archwire or other orthodontic appliance. Associated methods of manufacture and use are also disclosed.

According to one embodiment, an orthodontic force module assembly is provided that includes a hollow outer body, a plunger (or plunger rod), a spring (such as a compressible coil spring, elastomeric device, or biasing member), and a push rod that, when assembled and placed in the mouth of a patient, cooperate together to provide forces for use in treating class II and/or class III malocclusions. The force module assembly can be provided disassembled, partially assembled, or fully assembled as desired. In addition, once assembled, it can be partially disassembled if desired to facilitate installation within the mouth of a patient.

The hollow outer body has a hollow interior that extends between a proximal end and a distal end. The outer body also includes a proximal opening at the proximal end and a distal opening at the distal end that provide access to the hollow interior. The plunger is slidably positionable through and within the distal opening and hollow interior of the outer body. When assembled during use, at least a proximal end of the plunger is positioned within the hollow interior of the outer body. According to one embodiment, the proximal end of the plunger is enlarged compared to a main shaft. A distal end cap having a distal passageway smaller than the proximal end of the plunger can be placed at the distal end of the outer body to confine the proximal end of the plunger within the hollow interior of the outer body when assembled. The main shaft of the plunger can be slidably disposed through the distal passageway of the distal end cap during use.

The spring is positionable within the hollow interior of the outer body and, when assembled during use, the spring bears against the plunger and resists proximal movement of the plunger relative to the outer body. According to one embodiment, the spring bears against the proximal end of the plunger. As the plunger is moved proximally relative to the outer body, the spring is compressed, which provides a countervailing force that urges the plunger distally during use. A proximal end cap having a proximal passageway smaller than the spring can be placed at the proximal end of the outer body in order to confine the spring within the hollow interior of the outer body when assembled.

The push rod is slidably positionable through the proximal passageway of the proximal end cap and into hollow interior of the outer body so that at least a distal end of the push rod is positioned within the hollow interior of the outer body during use. According to one embodiment, the push rod can move independently of and does not engage with the spring. This permits free unbiased movement of the push rod in and out of the outer body during use. However, the push rod may include a detent, such as a stop, collar, protrusion, bend, or portion of varying diameter that cannot pass through the proximal passageway of the distal end cap. This limits distal movement of the push rod relative to the outer body during use. In this way, further distal movement of the push rod causes the outer body to move distally relative to the plunger and/or the plunger to move proximally relative to the outer body so as to compress the spring, which provides a countervailing force as noted above.

According to another embodiment, an assembled orthodontic force module is provided for use in correcting class II and/or class III malocclusions. The force module comprises a hollow outer body having a hollow interior extending between a proximal end and a distal end, a proximal opening at the proximal end, and a distal opening at the distal end. A plunger is at least partially slidably disposed through the distal opening and hollow interior of the outer body. A spring is positioned within the hollow interior of the outer body and bears against the plunger to resist proximal movement of the plunger relative to the outer body during use. A push rod is slidably positionable through the proximal opening and hollow interior of the outer body so that at least a distal end of the push rod being is positioned within the hollow interior of the outer body during use. The outer body, plunger, spring, and push rod can have features and cooperate together as discussed above relative to the orthodontic force module assembly.

According to other embodiments, orthodontic force modules and assemblies as disclosed herein can have other features, which can be provided separately or in combination. For example, the push rod can have a diameter so as to be slidably positionable through an axial passageway of the spring. The proximal end cap may further comprises a hollow distal extension that is positionable through the axial passageway of the spring in order to help support and prevent kinking during compression. The plunger can have an axial passageway configured to slidably receive a portion of the push rod as the spring is compressed beyond a certain point. In this way, the outer body, plunger, spring, and push rod can form a telescopic arrangement during use. The force module may be configured to provide a substantially smooth outer surface for patient comfort and that is substantially devoid of spaces or pockets where plaque or food debris can collect during use. The force module, including the outer body and plunger, can be low profile for reduced tissue damage.

One or more of the outer body, plunger, spring, and push rod may comprise at least one type of metal, such as stainless steel or other biologically compatible metal. According to another embodiment, at least some of the components of the orthodontic force modules may include a molded polymer material. To prevent fatigue and provide a spring that provides more reliable spring-back over time, the spring may comprise a Co—Cr—Ni alloy, such as Elgiloy®. According to one embodiment, the spring comprises a compressible coil spring.

The orthodontic force modules or assemblies as described herein may further include distal attachment means at or near a distal end of the plunger for attachment to a buccal tube or other orthodontic appliance and proximal attachment means disposed at or near a proximal end of the push rod for attachment to an arch wire and/or another appliance. The distal and proximal attachment means may comprise any attachment structures known and used in the art to attach orthodontic force modules to teeth. According to one embodiment, the distal attachment means may comprise a bendable wire or pin that can be inserted into an orthodontic headgear tube or buccal tube and bent around to fasten the plunger to the appliance.

The proximal attachment means at the proximal end of the push rod can include a hook (e.g., a "shepherd's hook") or other appropriate device or shape for slidable or fixed attachment to an orthodontic archwire or bracket attached to upper or lower teeth during use. If included, the shepherd's hook preferably has a bend relative to the axis of the push rod shaft that is less than 120°, more preferably less than about 115°, and most preferably less than about 110° (e.g., 105°). Alternatively, a rod with a hole or slot through a laterally extending flange can provide appropriate (e.g., slidable) attachment to an orthodontic archwire.

The orthodontic force modules can be used to correct either Class II or Class III malocclusions depending on how they are attached to a person's teeth. To correct Class II malocclusions, the distal end of the plunger can be attached to a molar of the upper teeth (or maxilla), such as by a buccal tube or other orthodontic appliance, and the proximal end is attached at or near a canine of the lower teeth (or mandible), such as by an archwire. To correct Class III malocclusions, the attachment is reversed such that the distal end of the plunger can be attached to a molar of the lower teeth (or mandible), such as by a buccal tube or other orthodontic appliance, and the proximal end is attached at or near a canine of the upper teeth (or maxilla), such as by an archwire. Of course, the foregoing is merely suggestive and not a limiting description of how a practitioner may choose to use the orthodontic force modules.

Another example of force module attachment means includes a latch mechanism. The latch mechanism includes a rigid body with means for attaching the rigid body to an end of an orthodontic force module, a pin member pivotally attached to the body and configured to be insertable into an orthodontic buccal tube or other orthodontic appliance, and a latch member on the body for selectively locking and unlocking the pin in a snap-fit relationship when selectively pivoted toward or away from the latch member. According to one embodiment, the latch member comprises a pair of spaced apart prongs that temporarily spread apart when the pin member is inserted or removed from the latch member. This device provides for an easier install and can provide an audible noise, which indicates that the clip as been attached or detached. The pin member advantageously has a length that is greater than a length of a passageway through an orthodontic buccal tube or other orthodontic appliance so that a distal portion of the pin member can extend beyond the passageway when inserted through the passageway in order to permit the distal portion of the pin member to be received by the latch member. One or more of the rigid body, pin member, and latch member may comprise one or more types of metal.

Orthodontic force module assemblies as disclosed herein may optionally further include one or more orthodontic buccal tubes or other orthodontic appliance, which are configured for attachment to a tooth and include a passageway for receiving a corresponding pin or wire attached to a distal end of the plunger. Orthodontic force module assemblies as disclosed herein may also optionally further include one or more orthodontic arch wires configured for attachment to orthodontic brackets on a person's teeth or bands attached to a person's molars. The force modules can provide a smooth outer surface for increased comfort and hygiene.

Another embodiment of the present disclosure is directed to a connector for coupling an orthodontic force module to a buccal tube of a molar bracket. The connector includes a generally L-shaped connector body including a buccal tube coupling leg forming a long leg of the L, while a force module coupling leg forms a short leg of the L. The buccal tube coupling leg extends from a distal end to which the force module coupling leg is attached towards a free proximal end. The distal end is referred to as "distal" as it corresponds to the distal end of the buccal tube with which the L-shaped connector is used. The proximal end of the buccal tube coupling leg corresponds to the proximal or mesial end of the buccal tube. The free proximal end is split, and also includes an enlarged locking protrusion so as to lock the buccal tube coupling leg within a buccal tube once the leg is fully inserted into the buccal tube.

The protrusion at the proximal end of the buccal tube coupling leg is sized so that it would not normally fit through the buccal tube, but because of the presence of the split, this enlarged portion of the leg is able to compress, allowing the protrusion to be introduced into the buccal tube. Once the protrusion exits the opposite end of the buccal tube, the compression of the protrusion at the proximal end of the leg is released so that the protrusion springs back to its original configuration, locking the buccal tube coupling leg to the buccal tube. The distal end of the buccal tube coupling leg may also include a protrusion of enlarged diameter which acts as a stop against further insertion of the buccal tube coupling leg into the buccal tube.

The force module coupling leg is rigidly attached to the distal end of the buccal tube coupling leg and extends generally laterally relative to the buccal tube coupling leg. The force module coupling leg may be diametrically smaller than the buccal tube coupling leg and its shaft is sized so as to be insertable through a hole formed through a flange near a distal end of a force module. The force module coupling leg may include an enlarged head rigidly attached to its free end opposite where the force module coupling leg is attached to the buccal tube coupling leg. Such an enlarged head can be used to lock the leg to a flange of the force module. According to one embodiment, the L-shaped connector body may be assembled from two separate pieces (i.e., the buccal tube coupling leg and the force module coupling leg) which are welded, soldered, brazed, or otherwise attached together. Prior to attachment of the two pieces together, the end of the force module coupling leg opposite the enlarged head may be inserted through a passageway in the flange of the force module, as the enlarged head is too large to pass through the flange passageway. Once the force module coupling leg is attached (e.g., laser welded) to the buccal tube coupling leg, the L-shaped connector is permanently and non-releasably coupled to the flange of the force module because the flange will be trapped between the enlarged head of the force module coupling leg on one end and the large diameter of the distal end of the buccal tube coupling leg on the other end.

In addition to the L-shaped connector body, the connector may further include an anti-rotation L-shaped stop. The L-shaped stop may also include two legs, a relatively short attachment leg that rigidly attaches the stop to the distal end of the buccal tube coupling leg, as well as a relatively longer buccal tube contacting leg having a free end that extends generally parallel to and in the same direction as the buccal tube coupling leg. The buccal tube contacting leg acts as a stop that contacts and prevents over-rotation of the connector body relative to the buccal tube of the molar bracket.

Another aspect of the present disclosure is directed to alternative connector assemblies for coupling a molar bracket to an orthodontic force module for use in a class II or class III correction procedure. The connector assembly comprises a connector body, a first coupling pin for coupling a buccal tube of a molar bracket to the connector body, and a second coupling pin for coupling a flange of an orthodontic force module to the connector body. The connector body includes a body, a buccal tube receiving recess formed into a gingival side of the body for receiving a buccal tube of a molar bracket, a flange receiving recess formed into an opposite side of the body for receiving a flange disposed at or near a distal end of the force module, a first channel disposed through the body that is axially aligned with the buccal tube receiving recess, and a second channel disposed through the body that is axially aligned with the flange receiving recess. In use, the first coupling pin is inserted into the first channel and the buccal tube, coupling the buccal tube to the connector body. The second coupling pin is similarly inserted into the second channel and through a hole formed through the flange near the distal end of the force module, coupling the flange of the force module to the connector body.

In one embodiment, the connector body may be formed of metal, plastic, or an elastomeric material. Manufacture from an elastomeric material (e.g., silicone) provides some unique benefits. Elastomeric materials exhibit very high flexibility and elasticity, which allows the connector body to bend, flex, and elastically deform as a result of movement of the force module and/or the patient's jaws. Such elasticity and flexibility is advantageous when the patient is repeatedly opening and closing his or her jaw, which is common in everyday activities (e.g., talking, eating, yawning, etc.). The connector assembly provides a dynamic but secure coupling between the force module and the molar bracket affixed to the patient's molar in which the orientation of the distal end of the force module relative to the connector body, and the connector body relative to the molar bracket, is able to spontaneously adjust to various jaw movements as the upper and lower jaws are moved relative to one another.

In this way, the force module and molar bracket are securely and indirectly coupled to one another, but the connector body still permits sufficient freedom of movement between the molar bracket (affixed to a molar of one jaw) and the force module (coupled at its proximal end to a bracket or arch wire of the other jaw). The coupling is indirect in that the force module is not directly coupled to the molar bracket, but through the connector body which acts as an interface between the force module and molar bracket. For example, the coupling mechanism allows the connector body to rotate inwardly and outwardly about a pin hinge structure at the buccal tube, and also allows the force module to rotate upwardly and downwardly about a pin hinge structure at the force module flange. Freedom of movement is particularly enhanced in embodiments where the connector body is formed of an elastomeric material, as the connector body itself is able to flex, elastically deform, and adapt as needed. Such an embodiment also provides an additional degree of comfort to the patient, as the elastomeric connector body presents a soft, smooth, elastomeric surface to the patient's tongue, cheek, and other tissues which it may contact.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. The drawings depict only typical embodiments of the invention and are not therefore to be considered limiting of its scope.

FIG. 4E is a perspective view illustrating the exemplary orthodontic force module or force module assembly of FIGS. 1A-1C with the push rod advanced distally relative to the outer body and the plunger fully advanced proximally relative to the outer body;

DETAILED DESCRIPTION OF THE PREFERRED EMBODIMENTS

I. Introduction

The present invention is directed to orthodontic force modules and force module assemblies for use in correcting class II and/or class III malocclusions. In one embodiment, the force module includes a hollow elongate body extending between a distal end and a proximal end; a plunger slidably positionable within the hollow elongate body; a spring (such as a compressible coil spring, elastomeric spring or spring like body, or other biasing member) that bears against the plunger to resist movement; and a push rod slidably positionable within the hollow elongate body.

When the orthodontic force module or assembly is attached between teeth of the upper and lower jaw (e.g., for class II correction), a distal end of the plunger may be attached to a posterior tooth (e.g., a molar) on the upper jaw (maxilla) while the proximal end of the push rod may be attached to a canine of the lower jaw, such as by means of archwire connection on mesial attachment (or mandible attachment). The spring provides an expansion force relative to the plunger and push rod in order for the orthodontic force module or assembly to apply corrective forces for correction of a class II correction.

The orthodontic force module of the assembly can be used to correct Class III malocclusions by configuring the force module so that the proximal end is attached to a canine of the upper jaw by an archwire connection on mesial attachment (or maxillary attachment) and the distal end is attached a posterior tooth (e.g., a molar) of the lower jaw (or mandible).

II. Exemplary Orthodontic Force Modules and Assemblies

Figure 1A:
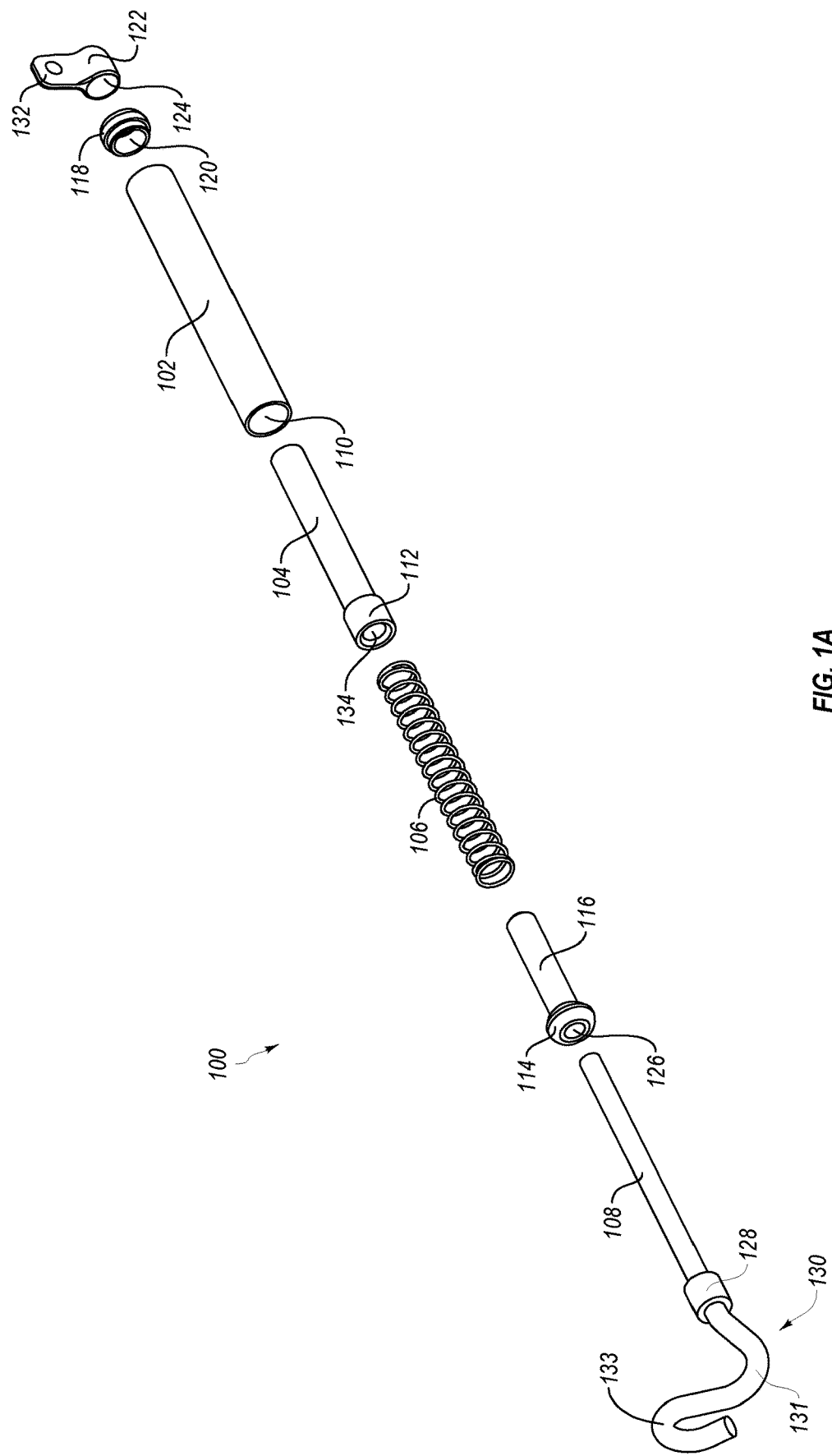
FIG. 1A is an exploded perspective view illustrating an exemplary embodiment of an exemplary orthodontic force module or force module assembly as disclosed herein.
Figure 1B:
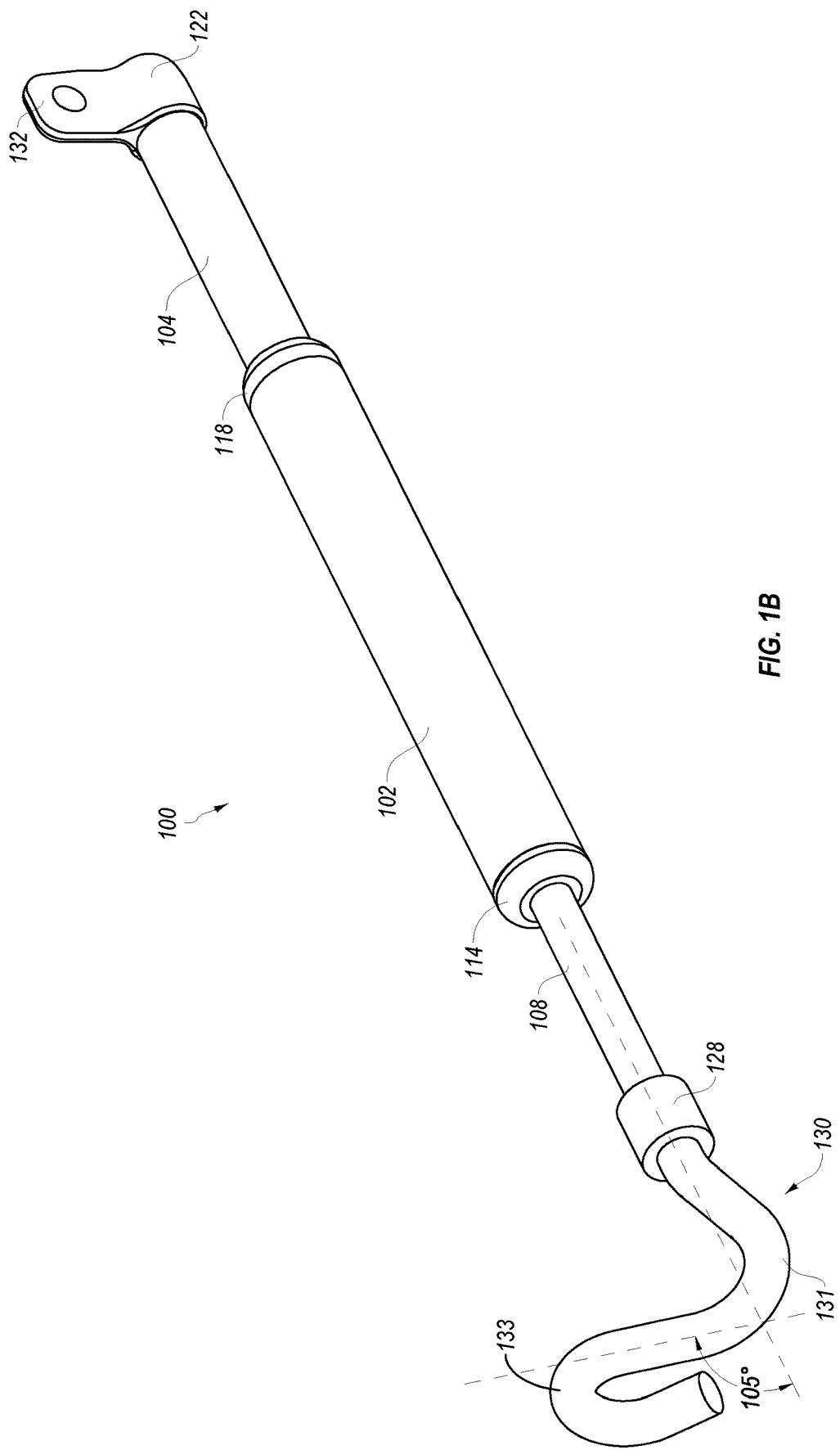
FIG. 1B is a perspective view illustrating the exemplary orthodontic force module or force module assembly of FIG. 1A assembled together.
Figure 1C:
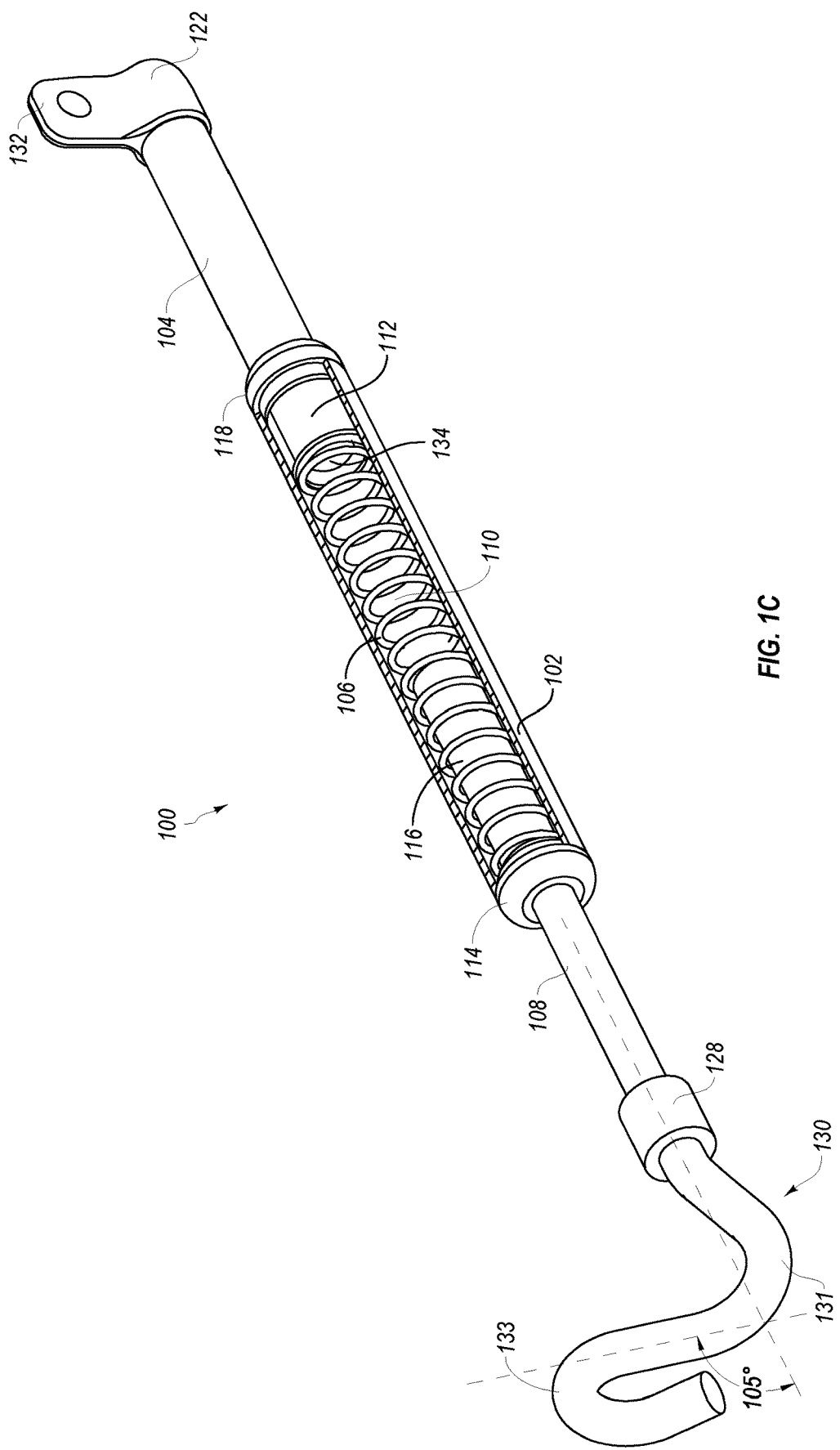
FIG. 1C is a cutaway view of the hollow outer body of the assembled orthodontic force module or force module assembly of FIG. 1B in order to illustrate a coil spring positioned within the hollow interior of the hollow outer body in extended condition.

Reference is now made to the drawings. FIGS. 1A-1C illustrate an exemplary embodiment of an exemplary orthodontic force module or force module assembly as disclosed herein for use in correcting Class II and/or Class III malocclusions. FIG. 1A is an exploded perspective view of an orthodontic force module or force module assembly 100. Force module or assembly 100 includes an elongate hollow outer body 102, a plunger 104 (which can be embodied or exemplified as a rod or plunger rod), a compressible coil spring 106, and a push rod 108 that are configured to fit together in a telescopic configuration when assembled during use, as shown in FIGS. 1B and 1C.

Returning to FIG. 1A, elongate hollow outer body 102 extends between proximal and distal ends and includes a hollow interior 110 that opens at proximal and distal ends of outer body 102. Outer body 102 is shown having a substantially circular cross section so as to substantially cylindrical but could have other cross sectional shapes as desired (e.g., oval, square, triangular, etc.). Hollow interior 110 of outer body 102 has a diameter sufficiently large so that at least a portion of plunger 104, coil spring 106, and push rod 108 can be positioned within hollow interior 110 of outer body 102 when assembled together.

According to one embodiment, plunger 104 further includes an enlarged proximal end portion 112 that is enlarged compared to the shaft of plunger 104 extending distally from proximal end portion 112. A distal end cap 118 having a distal passageway 120 attaches to, or is integrally formed together as a single piece with, the distal end of outer body 102 and cooperates with plunger 104 when assembled to permit slidable movement of plunger 104 relative to outer body 102 while confining proximal end portion 112 within the hollow interior 110 of outer body 102 when assembled. In particular, distal passageway 120 is advantageously smaller than enlarged proximal end portion 112 so as to block passage of proximal end portion 112 through distal passageway 120 but large enough to receive and permit slidable movement of the shaft of plunger 104 when assembled and during use.

A proximal end cap 114, which may have a hollow distal extension 116, and a proximal passageway 126 attaches to the proximal end of outer body 102 in order to confine coil spring 106 within hollow interior 110 of outer body 102 when assembled. Hollow distal extension 116 is inserted through a proximal section of coil spring 106 when assembled, which may support and prevent kinking of coil spring 106 when compressed during used.

Proximal end cap 114 also cooperates with push rod 108 when assembled to permit slidable movement of push rod 108 relative to outer body 102 during use. The distal end and shaft of push rod 108 are smaller than proximal passageway 126 of proximal end cap 114 so as to permit slidable movement of push rod 108 relative to outer body 102. Push rod 108 further includes a collar 128 or other detent member (e.g., a protrusion or bend) that limits distal movement of push rod 108 relative to outer body 102. In this embodiment, push rod 108 does not engage with and therefore moves without being directly biased by coil spring 106. In this way, push rod 108 can freely slide proximally and distally relative to outer body 102 until collar 128 or another detent member makes abutment with proximal end cap 114 and/or the proximal end of outer body 102. The distal end of push rod 108 can also be freely inserted through and withdrawn from proximal passageway 126 of proximal end cap 114. Nevertheless, push rod 108 may optionally include an enlarged distal end (not shown) to limit proximal movement and withdrawal of push rod 108 from hollow interior of outer body 102. Distal movement of push rod 108 causes the distal end of push rod 108 to extend beyond distal extension 116 of proximal end cap 114, through an axial passageway through coil spring 106, and approach proximal end 112 of plunger 104. The push rod 108 and plunger 104 are brought closer together as the coil spring 106 is compressed. According to the embodiment shown in FIG. 1A, plunger 104 further includes a hollow passageway 134 therethrough that permits push rod 108 to be telescopically received within plunger 104 during use to permit further compression of force module or assembly 100 depending on the force applied by the patient's jaw relative to the counter force exerted by the coil spring 106.

Force module or assembly 100 further includes a hook 130 or other attachment device extending from a proximal end of push rod 108 for use in attaching push rod 108 to an orthodontic bracket or archwire during use in correcting a Class II and/or Class III malocclusion. An end piece 122 configured to fit onto the distal end of plunger 104 carries a flange 132 or other means for use in attaching the plunger 104 to an orthodontic bracket during use. In this embodiment, end piece 122 has a recess 124 therethrough that is sized and configured to fit over the distal end of plunger 104. End piece 122 also includes a passage that permits push rod 108 to pass therethrough.

As illustrated in FIG. 1A, hook 130 is a "shepherd's hook" having a main curved section 131 extending beyond collar 128 and having a bend angle, or angle of curvature, relative to the longitudinal axis of push rod 108. The angle of the main curved section 131 of hook 130 can have an angle that is less than 120°, less than about 117.5°, less than about 115°, less than about 110°, less than about 105°, or less than about 100°. Hook 130 can further include an auxiliary bend 133, which can wrap around to as to lock the hook in a slidable configuration relative to an archwire attached to a person's teeth during use. In this configuration, the orthodontic force module can be used to correct both Class II and III malocclusions depending on how the device is attached to the person's teeth.

FIGS. 1B and 1C are perspective views that show exemplary orthodontic force module or force module assembly 100 of FIG. 1A assembled together. FIG. 1C further shows a cutaway view of outer body 102 in order to reveal coil spring 106 in extended condition within hollow interior 110 of outer body 102. As shown in FIGS. 1B and 1C, outer body 102, plunger 104, compressible coil spring 106, and push rod 108 fit together in a telescopic configuration when assembled. In the configuration shown in FIGS. 1B and 1A, a portion of push rod 108 is inserted partially through proximal passageway 126 of proximal end cap 114.

Push rod 108 is able to slide within proximal passageway 126 and hollow interior 110 without interference or force being applied by coil spring 106 until collar 128 abuts proximal end cap 114. In this way, slidable movement of push rod 108 relative to outer body 102 does not cause force module or assembly 100 to exert significant orthodontic forces until collar 128 abuts proximal end cap 114 and coil spring 106 is caused to become compressed by cooperative interaction between collar 128, proximal end cap 114, coil spring 106, and proximal end 112 of plunger 104. In addition, push rod 108 can be withdrawn entirely from proximal passageway 126 of end cap 114 and hollow interior 110 of outer body 102. This can facilitate installation to and/or removal of orthodontic force module or force module assembly 100 from a jaw of a patient.

Figure 2A:
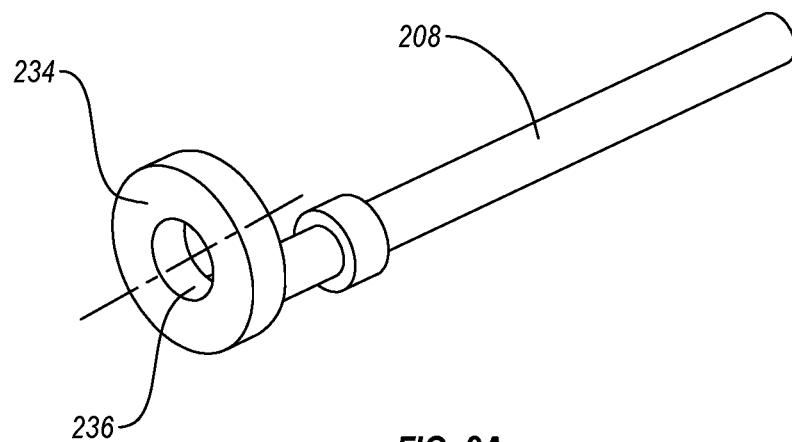
FIGS. 2A-2C illustrate an alternative embodiment of a push rod for use in the disclosed force modules and force module assemblies having alternative structure or means for attachment to an archwire or other orthodontic appliance.
Figure 2B:
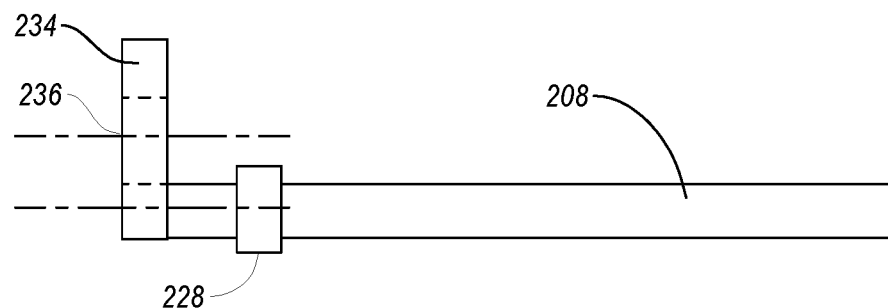
Figure 2C:
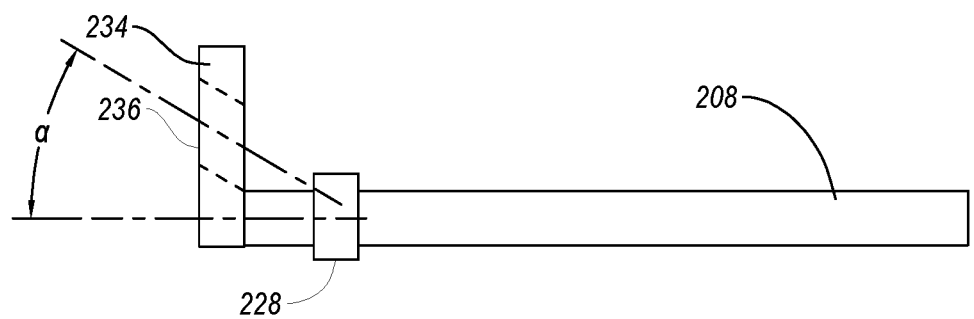

FIGS. 2A-2C illustrate an alternative embodiment of a push rod 208 for use in the disclosed force modules and force module assemblies having alternative structure or means for attachment to an archwire or other orthodontic appliance. A collar or detent 228 can be included to limit distal movement of push rod 208. As shown, rather than including a hook, such as a shepherd's hook 130 as in push rod 108, push rod 208 includes a laterally extending flange 234 having a hole 236 therethrough large enough to permit passage of an archwire. Hole 236 can have any desired or appropriate angle, such as a hole defined by walls that are essentially parallel to the longitudinal axis of push rod 208, as illustrated in FIG. 2B, or a hole defined by walls that are angled relative to the longitudinal axis of push rod 208, as illustrated in FIG. 2C. According to one embodiment, the angle α of hole 236 can be selected depending on the angle of the push rod 208 relative to an archwire on a patient's teeth when the force module is in use. For example, if a hole that is parallel to the axis of push rod 208 is understood to be 0°, an angled hole 236 will typically be greater than 0° and less than 90° and can be in a range of about 5° to about 90°, or about 7.5° to about 80°, or about 10° to about 70°, or about 15° to about 65°, or about 20° to about 60°.

Figure 3A:
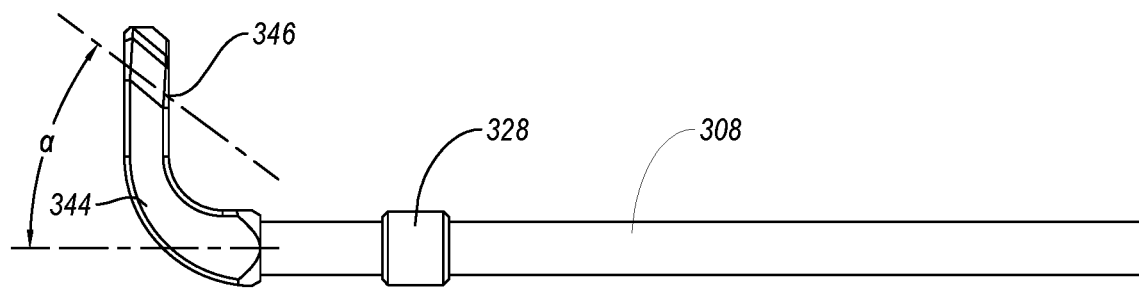
FIGS. 3A and 3B illustrate another embodiment of a push rod for use in the disclosed force modules and force module assemblies having alternative structure or means for attachment to an archwire or other orthodontic appliance.
Figure 3B:
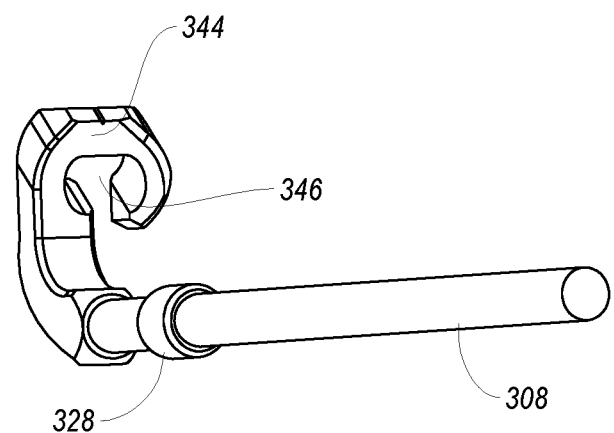

FIGS. 3A and 3B illustrate another alternative embodiment of a push rod 308 for use in the disclosed force modules and force module assemblies having alternative structure or means for attachment to an archwire or other orthodontic appliance. A collar or detent 328 can be included to limit distal movement of push rod 308. As shown, rather than including a hook, such as shepherd's hook 130 as in push rod 108 or a flange with a hole as in push rod 208, push rod 308 includes a laterally extending flange or extension 344 having a slot 346 therethrough large enough to permit passage of an archwire therethrough. Slot 346 can have any desired or appropriate angle relative to the longitudinal axis of push rod 308, as illustrated in FIG. 3B. According to one embodiment, the angle α of slot 146 can be selected depending on the angle of the push rod 308 relative to an archwire on a patient's teeth when the force module is in use. For example, if a slot that is parallel to the axis of push rod 308 is understood to be 0°, an angled slot 346 will typically be greater than 0° and less than 90° and can be in a range of about 5° to about 90°, or about 7.5° to about 80°, or about 10° to about 70°, or about 15° to about 65°, or about 20° to about 60°.

FIGS. 4A-F illustrate an exemplary orthodontic force module or force module assembly 400 similar to force module or force module assembly 100 illustrated in FIGS. 1A-1C in various positions and stages of compression as push rod 408 advances distally relative to outer body 402 and plunger 404 advances proximally relative to outer body 402.

Figure 4A:
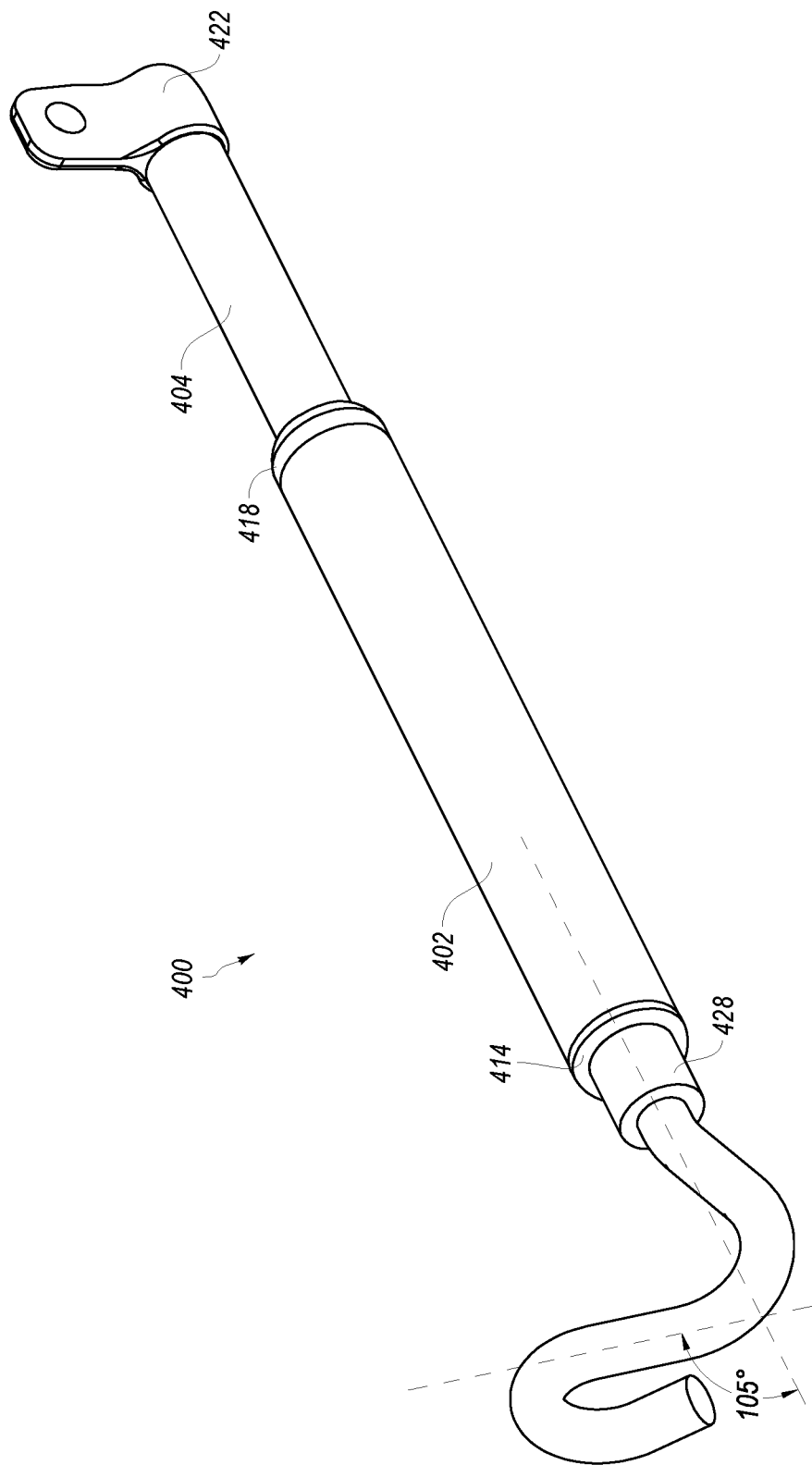
FIG. 4A is a perspective view illustrating the exemplary orthodontic force module or force module assembly of FIGS. 1A-1C with the push rod advanced distally relative to the outer body.
Figure 4B:
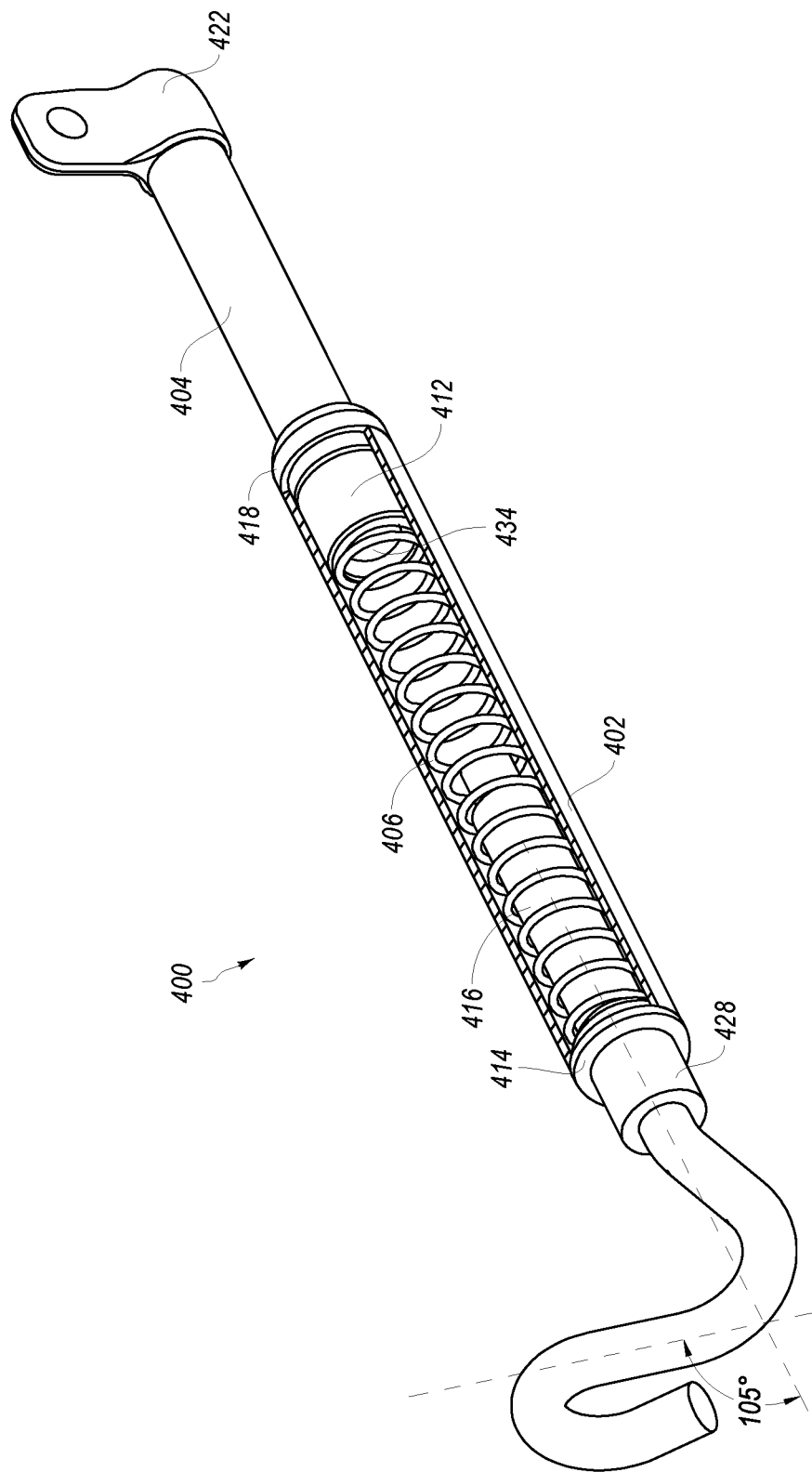
FIG. 4B is a cutaway view of the hollow outer body of the orthodontic force module or force module assembly of FIG. 4A in order to illustrate the coil spring positioned within the hollow interior of the hollow outer body in extended condition.

FIGS. 4A and 4B show a configuration of orthodontic force module or force module assembly 400 in which push rod 408 has been fully inserted distally relative to outer body 402 so that collar 428 makes abutment with proximal end cap 414. As best seen in FIG. 4B, coil spring 406 remains in an extended configuration within outer body 402 because distal movement of push rod 408 relative to outer body 402 does not by itself cause coil spring 406 to be compressed (or become more compressed if coil spring 406 is already partially compressed when in the fully extended configuration within outer body 402) until collar 428 makes abutment with proximal end cap 414. Push rod 408 is shown passed through distal extension 416 of proximal end cap 414 so that the distal end of push rod 408 extends through an axial passageway through coil spring 406. As will be shown below, further compression of force module or force module assembly 400 and coil spring 406 causes the distal end of push rod 408 to be telescopically received within passageway 434 of plunger 404.

Figure 4C:
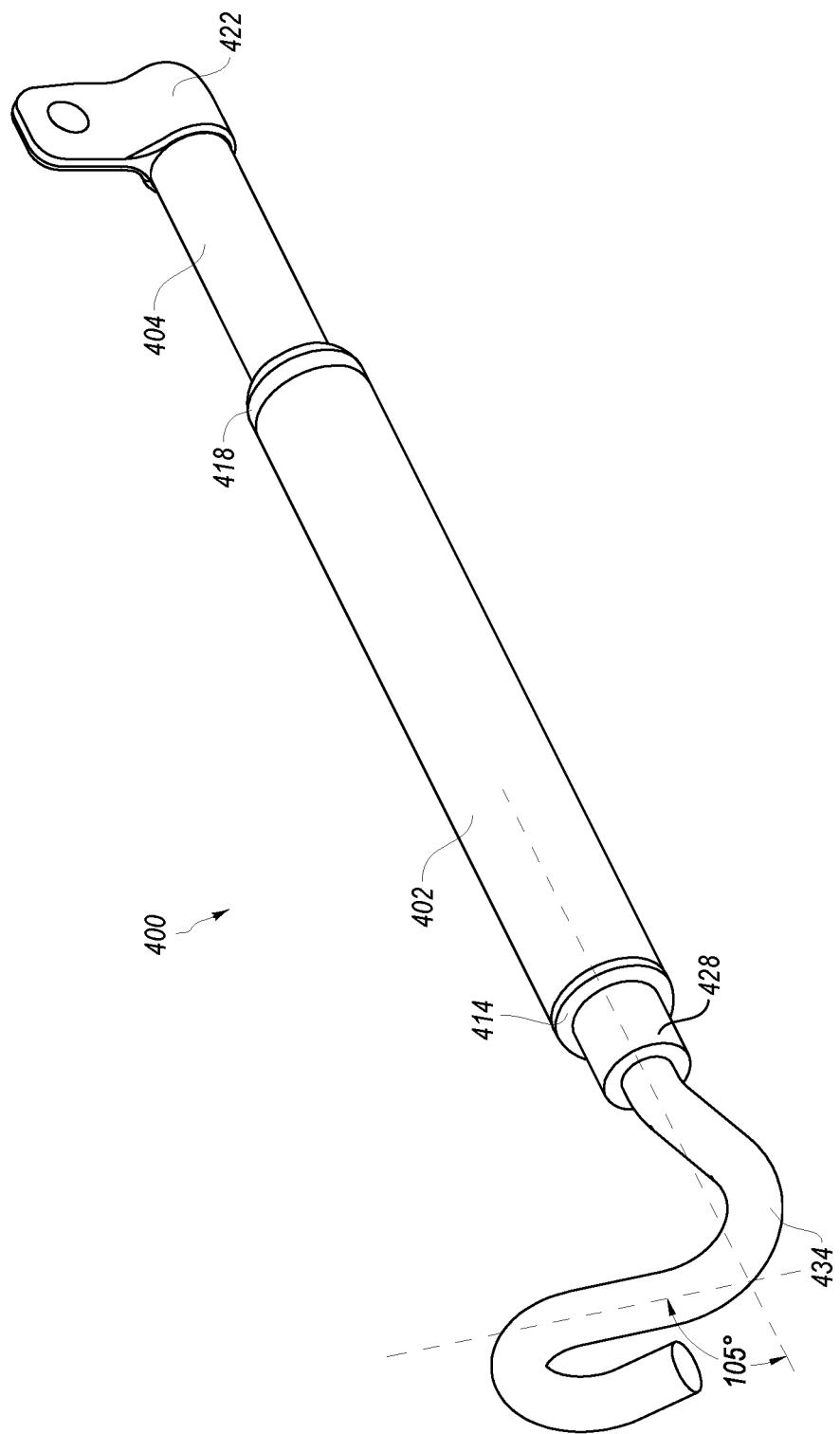
FIG. 4C is a perspective view illustrating the exemplary orthodontic force module or force module assembly of FIGS. 1A-1C with the push rod advanced distally relative to the outer body and the plunger partially advanced proximally relative to the outer body.
Figure 4D:
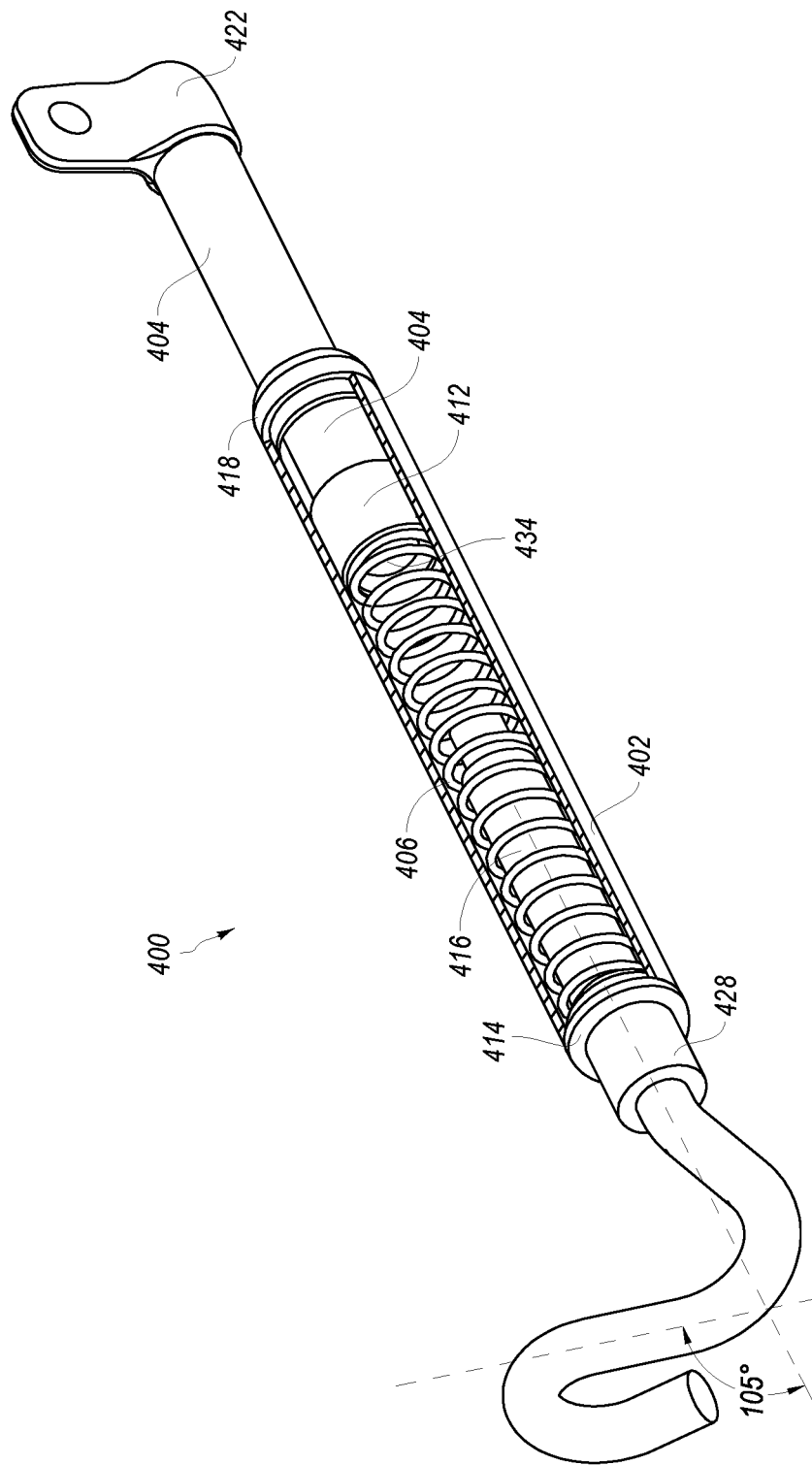
FIG. 4D is a cutaway view of the hollow outer body of the orthodontic force module or force module assembly of FIG. 4C in order to illustrate the coil spring positioned within the hollow interior of the hollow outer body in a partially compressed condition.

FIGS. 4C and 4D show a configuration of orthodontic force module or force module assembly 400 in which push rod 408 has been fully inserted distally relative to outer body 402 so that collar 428 makes abutment with proximal end cap 414 and so that, in addition, plunger 404 has been partially moved proximally relative to outer body 402. As best seen in FIG. 4D, coil spring 406 is partially compressed within outer body 402 between proximal end cap 414 and proximal end portion 412 of plunger 404. This partial compression (or further compression) of coil spring 406 results in the exertion of a countervailing force against proximal end cap 414 and proximal end portion 412 of plunger 404 that resists proximal movement of plunger relative to outer body 402 and urges plunger 404 distally relative to outer body 402. The force exerted by coil spring 406 against proximal end portion 412 of plunger 404 and proximal end cap 414 can vary depending on the strength of the spring 406 and the amount to which it has been compressed. The force applied by the coil spring 406 is directly related (or essentially equal) to the forces applied by orthodontic force module or force module assembly 400, through the plunger 404 and push rod 408, to the teeth to which they are attached.

Figure 4F:
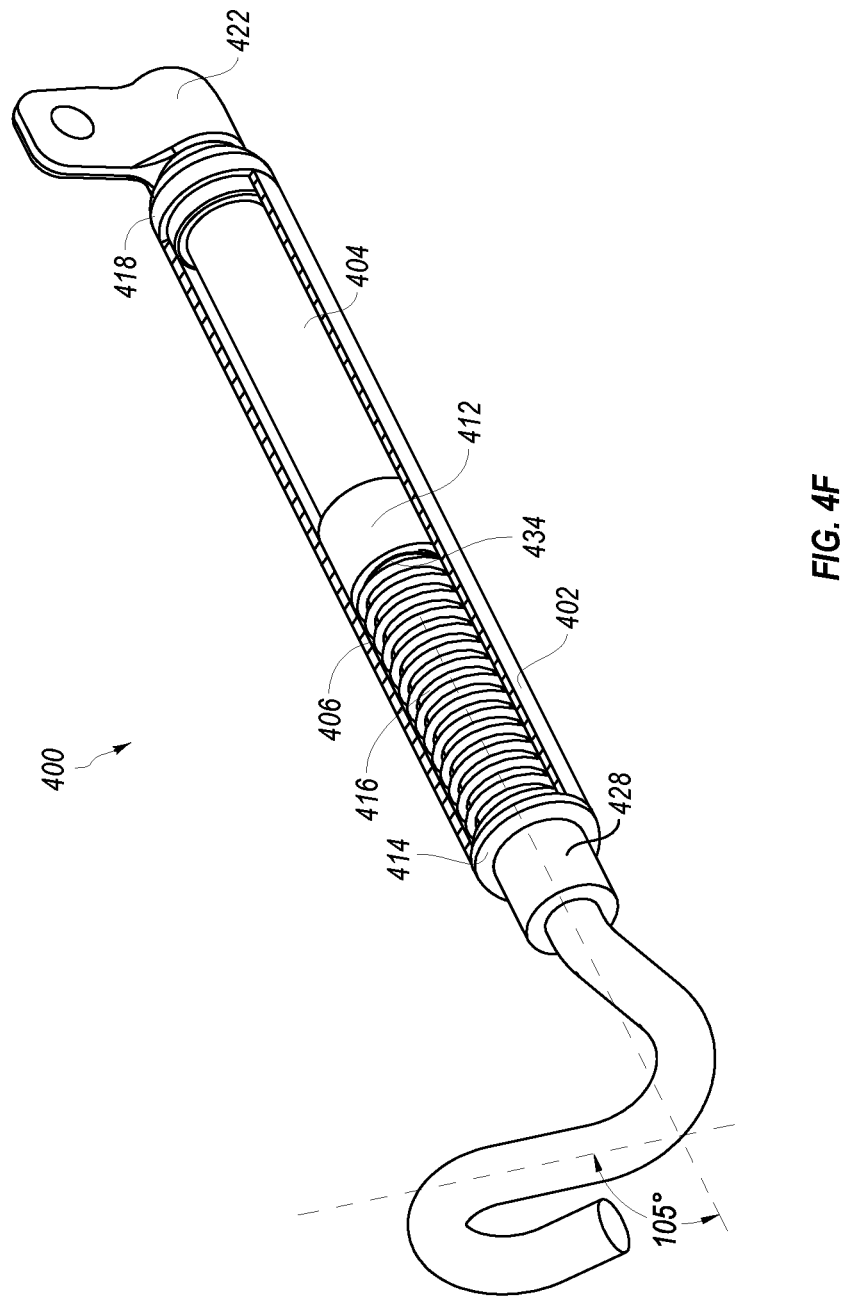
FIG. 4F is a cutaway view of the hollow outer body of the orthodontic force module or force module assembly of FIG. 4E in order to illustrate the coil spring positioned within the hollow interior of the hollow outer body in a substantially fully compressed condition.

FIGS. 4E and 4F show a configuration of orthodontic force module or force module assembly 400 in which push rod 408 has been fully inserted distally relative to outer body 402 so that collar 428 makes abutment with proximal end cap 414 and so that, in addition, plunger 404 has been fully moved proximally relative to outer body 402 so that end piece 422 makes abutment with distal end cap 418 and/or the distal end of outer body 402. Alternatively, end piece 422 can stop short of end cap 418 (e.g., so as to avoid overstressing the joint between end piece 422 and plunger 404) by abutment of distal extension 416 of end cap 414 to proximal end 412 of plunger 404 (e.g., so that distal extension 416 has a length and diameter so as to abut rather than pass through or terminate shy of proximal end 412).

As best seen in FIG. 4F, coil spring 406 is highly (or maximally) compressed within outer body 402 between proximal end cap 414 and proximal end portion 412 of plunger 404. Depending on the relative lengths of outer body 402, plunger 404, and push rod 408, end piece 422 may include a distal recess therethrough for permitting passage of the distal end of push rod 408 therethrough. In actual use, the coil spring 406 may or may not become fully compressed such that the amount of compression shown in FIGS. 4E and 4F may be illustrative only. The high compression of coil spring 406 results in maximum countervailing force being exerted against proximal end cap 414 and proximal end portion 412 of plunger 404 that urges plunger 404 distally relative to outer body 402. As before, the force exerted by coil spring 406 against proximal end portion 412 of plunger 404 and proximal end cap 414 can vary depending on the strength of the spring 406 and the amount to which it has been compressed. In addition, the expansion force applied by the coil spring 406 is to directly related (or essentially equal) to the forces applied by orthodontic force module or force module assembly 400, through the plunger 404 and push rod 408, to the teeth to which they are attached.

Figure 5A:
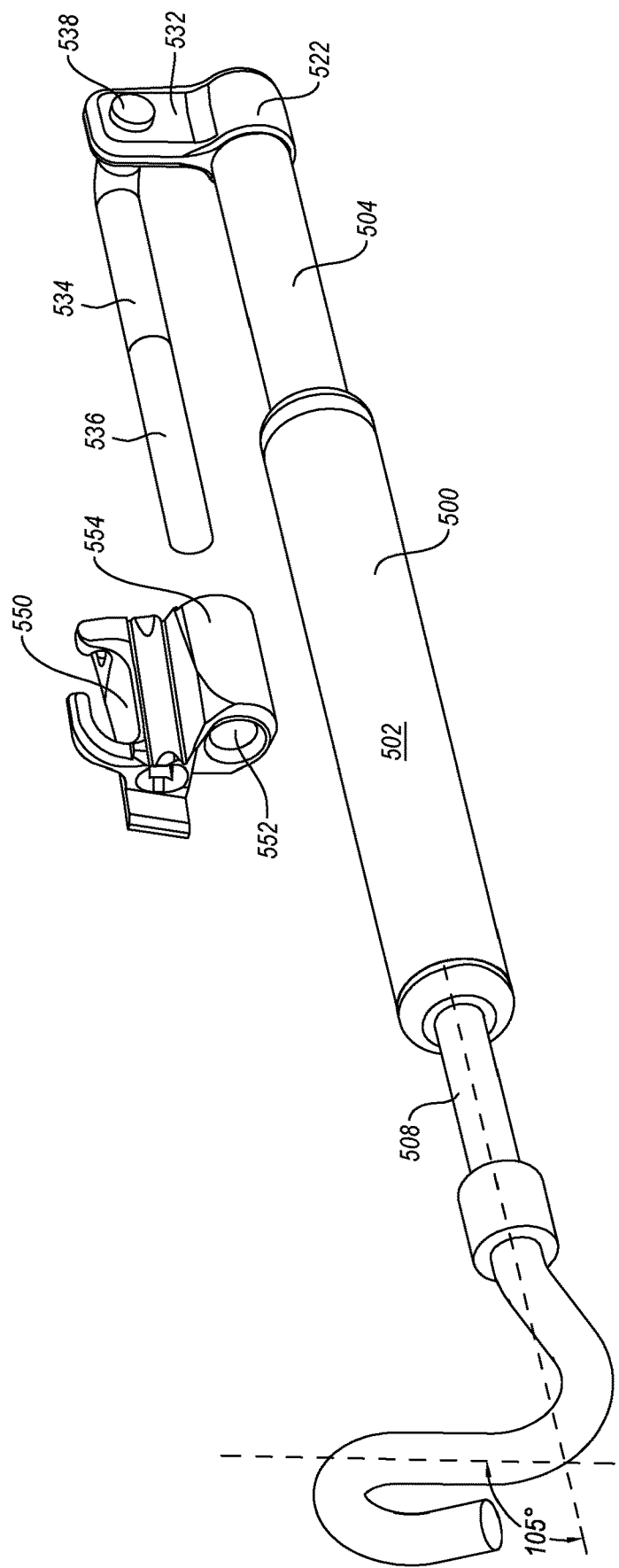
FIGS. 5A-5E are perspective views illustrating an orthodontic force module or force module assembly in which a pin is used to attach an end of the force module or assembly to an orthodontic buccal tube.

FIGS. 5A-5E are perspective views illustrating an orthodontic force module or force module assembly as disclosed herein in which a pin attachment member is used to attach an end of the force module or assembly to an orthodontic buccal tube. As shown in FIG. 5A, an orthodontic force module or force module assembly 500 includes an outer body 502, a plunger 504, a coil spring (not shown) within the hollow interior of outer body 502, and a push rod 508. These may cooperate in the same or different manner as in the embodiment shown in FIGS. 1-4.

Force module or assembly 500 further includes an end piece 522 positioned at the distal end of plunger 504 with a flange 532 or other means for use in attaching plunger 504 to an orthodontic bracket during use. In this embodiment, a pin 534 is used to attach plunger 504 to buccal tube 550. Pin 534 includes a distal end 536 for insertion through a longitudinal passageway 552 through a tube 554 of buccal tube 550. Pin 534 also includes a proximal end 538 that is pivotally attached to flange. In the illustrated embodiment, proximal end 538 is shown positioned through a corresponding hole in flange 532. Proximal end 538 of pin 534 may include an enlarged head on a proximal side of flange 532 to prevent withdrawal of pin 534 from the hole in flange 532. Proximal end 538 of pin 534 as shown also includes a bend on a distal side of flange 532 to prevent further insertion of pin 534 into the hole in flange 532. In this way, the bend and the enlarged head in proximal end 538 of pin cooperate with flange 532 to retain pin 534 in a desired, non-removable, yet pivoting attachment to flange 532. The pivoting aspect of pin 534 permits rotational movement of force module or assembly 500 relative to buccal tube 550 during use.

Figure 5B:
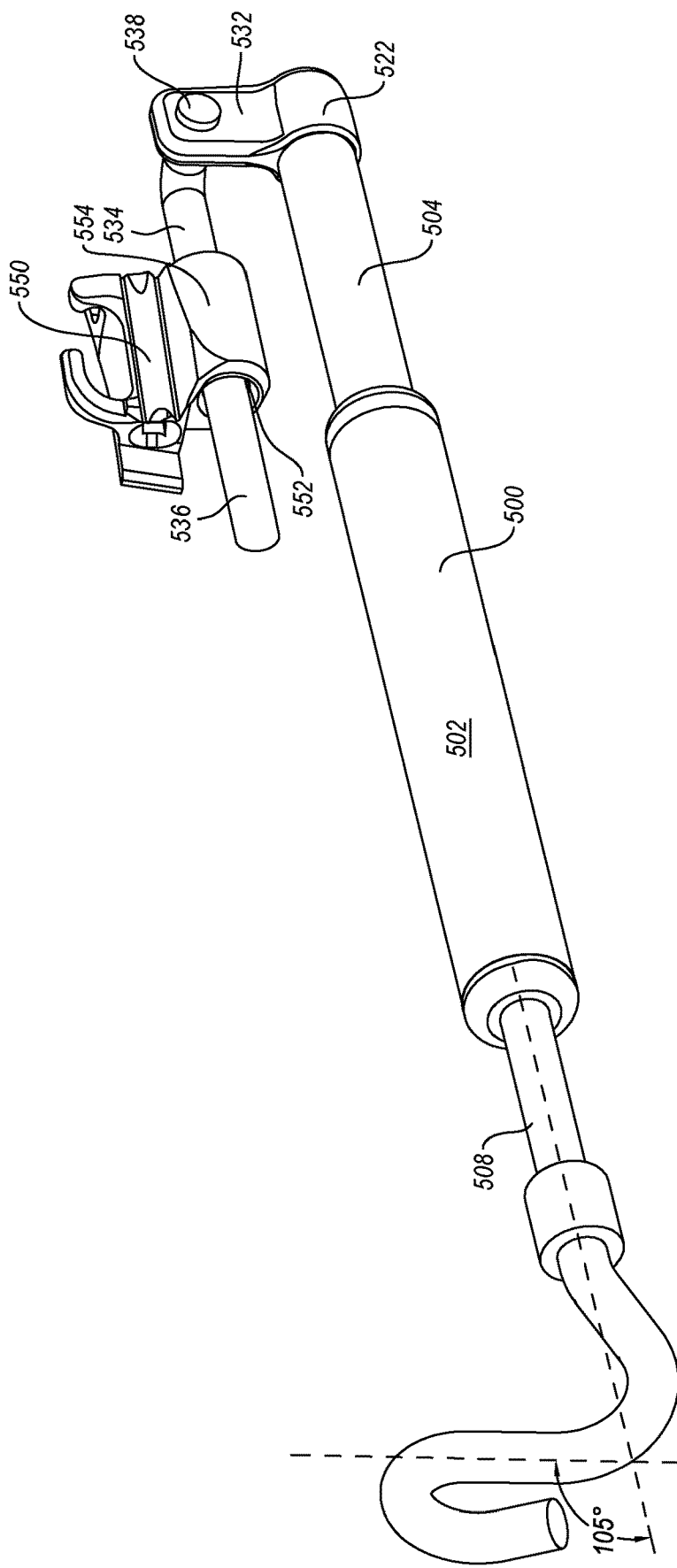
Figure 5C:
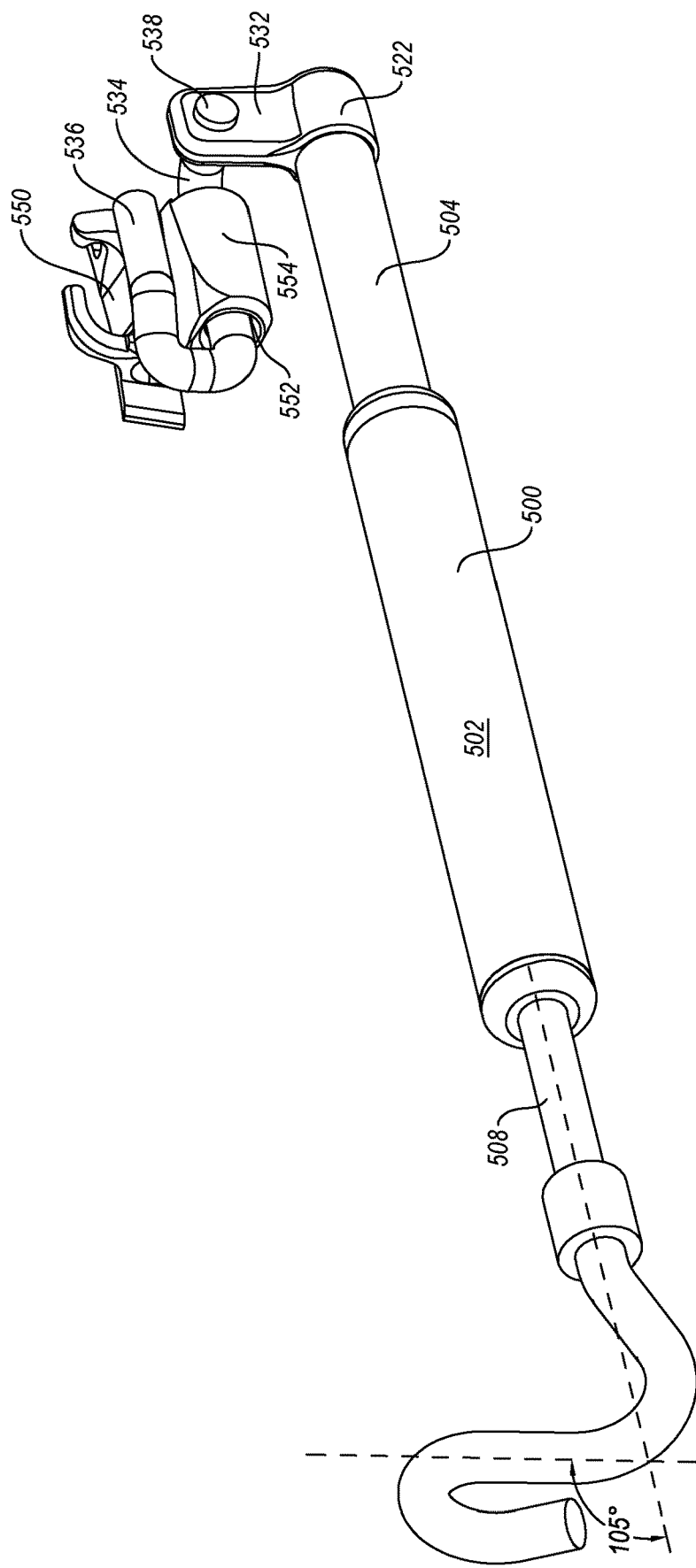

As shown in FIG. 5B, pin 534 is inserted through longitudinal passageway 552 of tube 554 until distal end 536 emerges through and beyond tube 534. Thereafter, and as shown in FIG. 5C, distal end 536 of pin 534 is bent around tube 534 in order to securely attach pin 534 to buccal tube 550. To remove force module or assembly 500 from buccal tube 550, distal end 536 is bent back into a substantially straight configuration and/or other position sufficient to permit withdrawal of distal end 536 of pin 534 from tube 534.

Figure 5D:
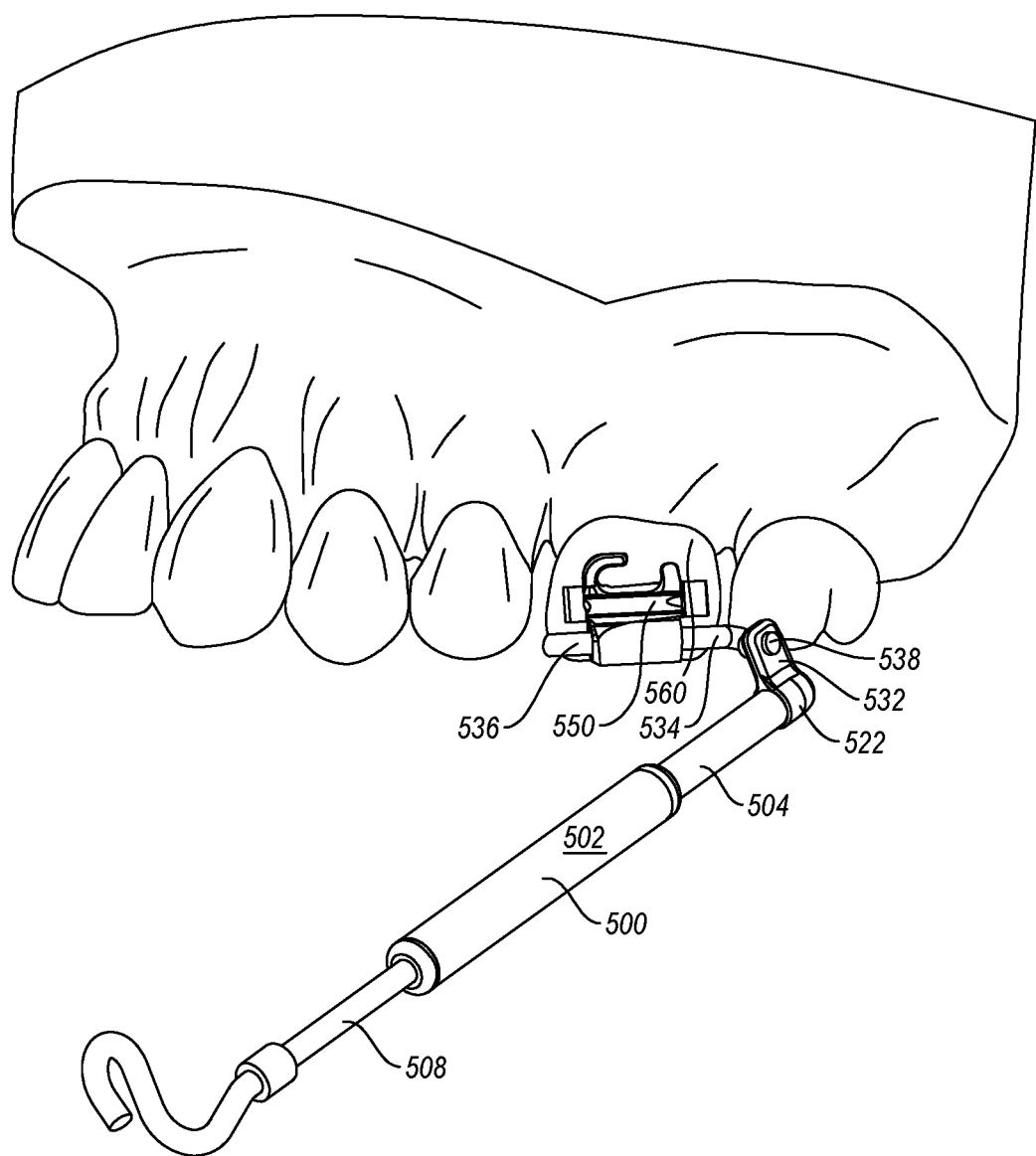
Figure 5E:
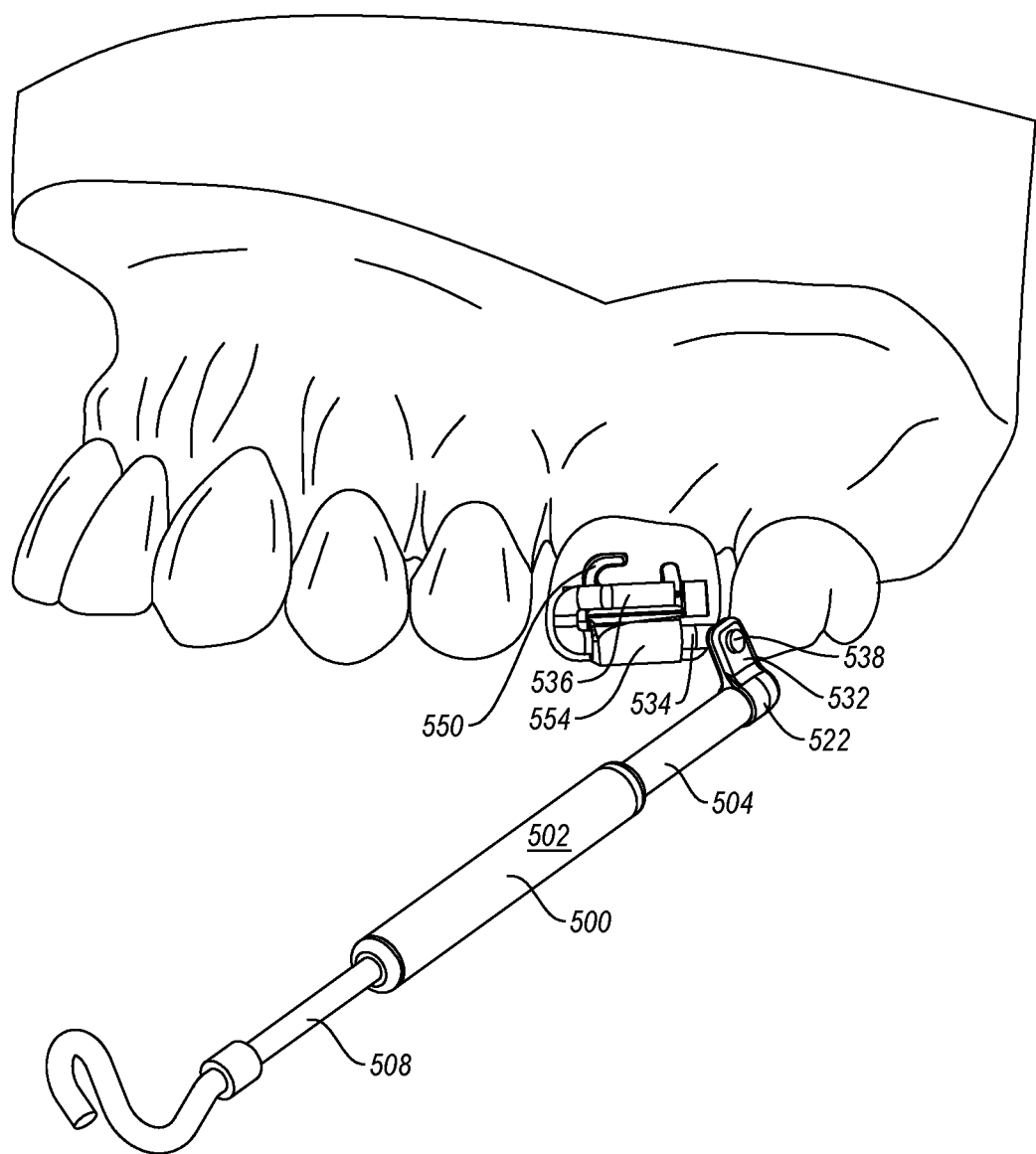

FIGS. 5D and 5E show force module or assembly 500 being attached to buccal tube 550 when attached to a patient's tooth 560. As shown in FIG. 5D, distal end 536 of pin 534 is inserted through the tube of buccal tube 550. The pivoting attachment of proximal end 538 of pin 534 permits rotation of force module or assembly 500 during placement so as to facilitate the procedure. As shown in FIG. 5E, plunger 504 of force module or assembly 500 is secured to buccal tube 550 by bending distal end 536 of pin 534 around the tube of buccal tube 550.

Figure 6A:
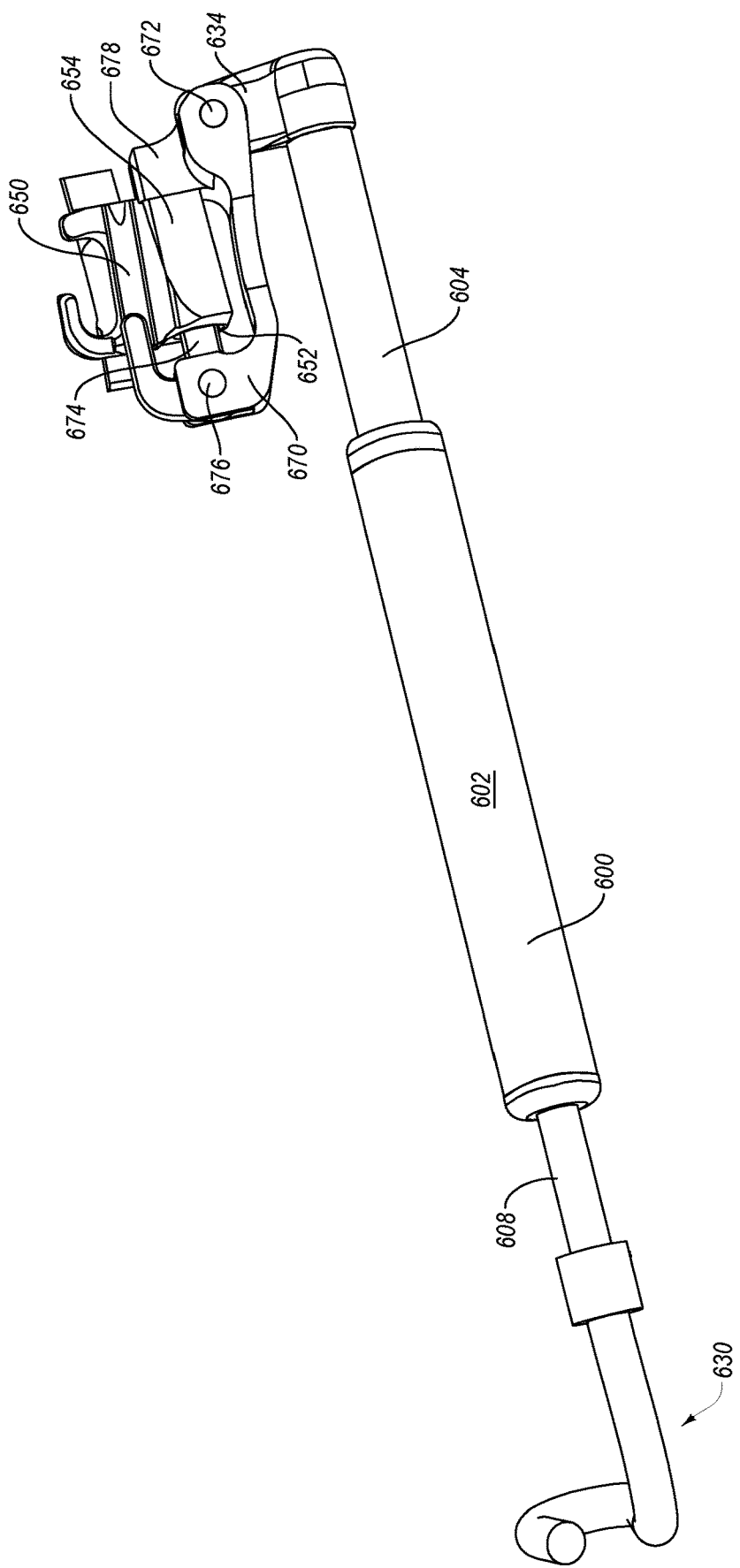
FIGS. 6A-6D are perspective views illustrating an orthodontic force module or force module assembly with a latch mechanism used to attach an end of the force module or assembly to an orthodontic buccal tube.

III. Exemplary Latch Mechanism for Selective Attachment and Release of an Orthodontic Force Module or Assembly to a Buccal Tube FIGS. 6A-6D are illustrate an exemplary latch mechanism used to selectively attach and detach an end of an orthodontic force module or force module assembly 600 to a buccal tube 650. As shown in FIG. 6A, force module or assembly 600 includes an outer body 602, a plunger 604, a coil spring (not shown) within the hollow interior of outer body 602, and a push rod 608. A hook 630 extending from a proximal end of push rod 608 and a flange 634 extending from a distal end of plunger 604 are used in attaching force module or assembly 600 to a patient's jaw during a procedure to correct a Class II or Class III malocclusion.

As further illustrated, the latch mechanism includes a main latch body 670 attached to flange 634 as shown by a first pivot connection or structure 672. A pivot pin 674 is pivotally connected to latch body 670 by a second pivot connection or structure 676. A latch member 678 includes a pair of spaced apart prongs with a space therebetween. Alternatively, the latch member can be a single prong or clip. Latch member 678 permits pivot pin 674 to be received and selectively locked between the prongs of latch member 678 (or adjacent to single prong clip) in a snap-fit relationship when rotated toward latch member 678, as illustrated in FIG. 6A. Pivot Pin 674 can be selectively unlocked from latch member 678 when sufficient force is applied to overcome the snap-fit relationship and pivot pin 674 is rotated away from latch member 678.

Figure 6B:
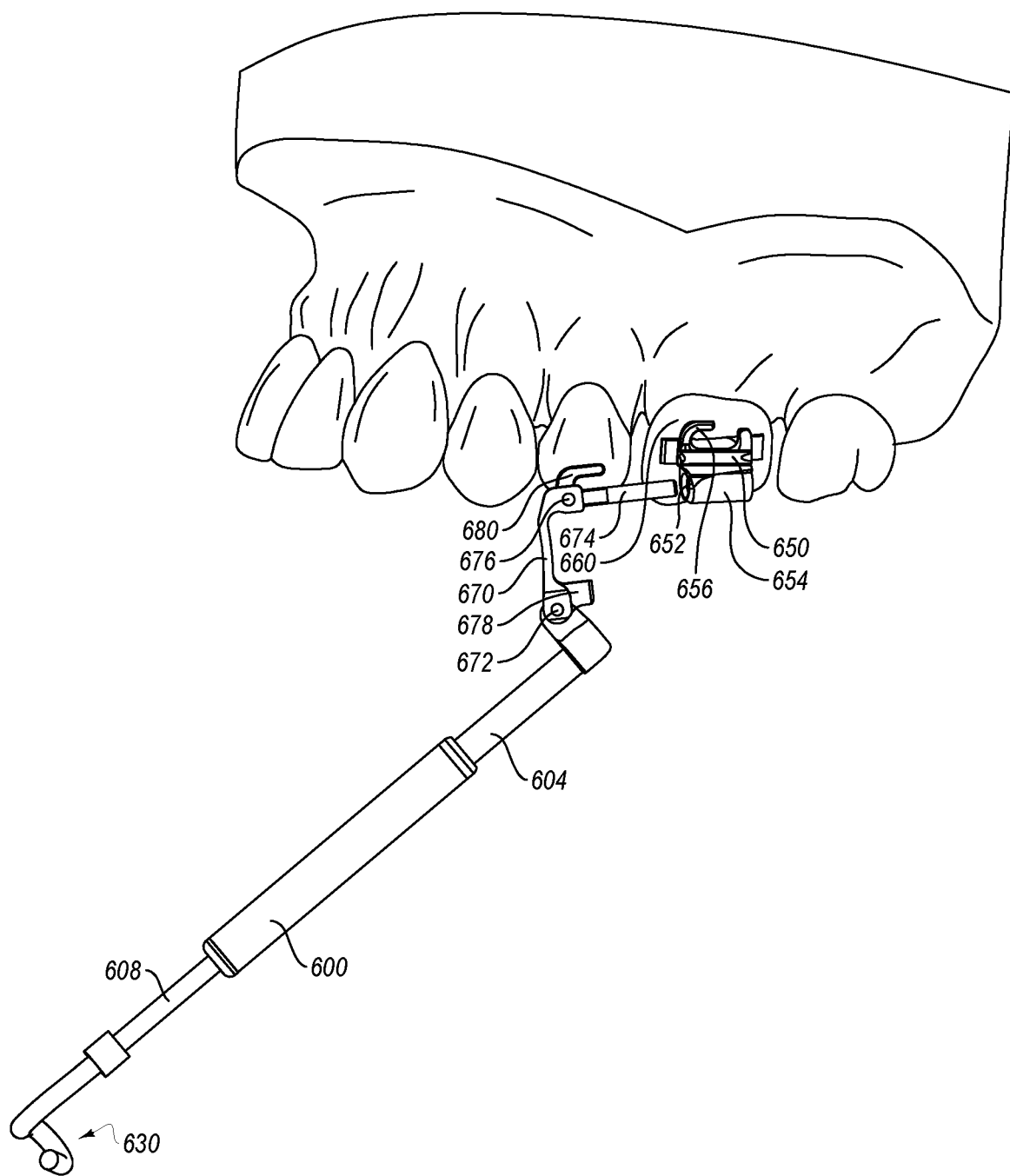
Figure 6C:
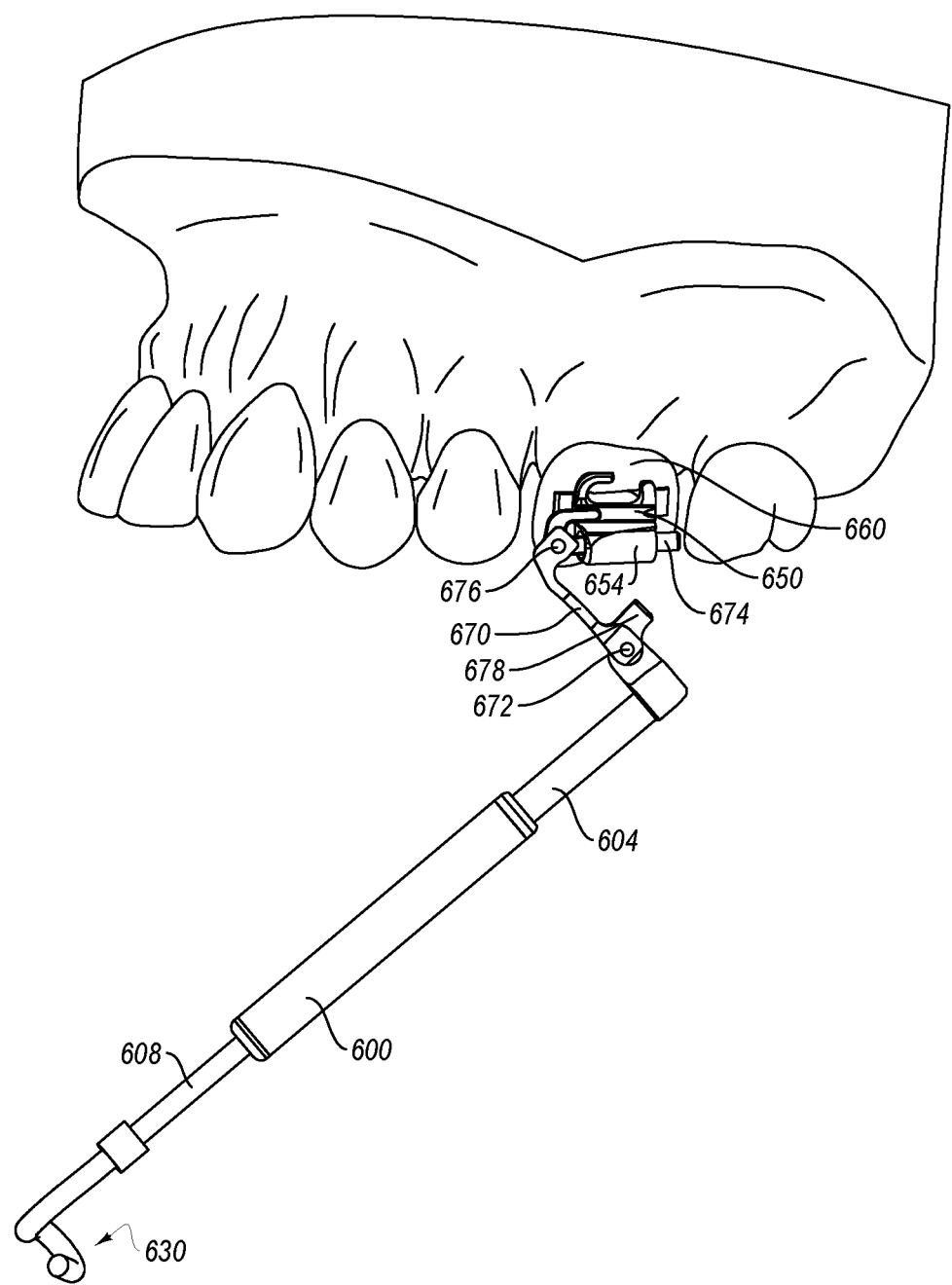
Figure 6D:
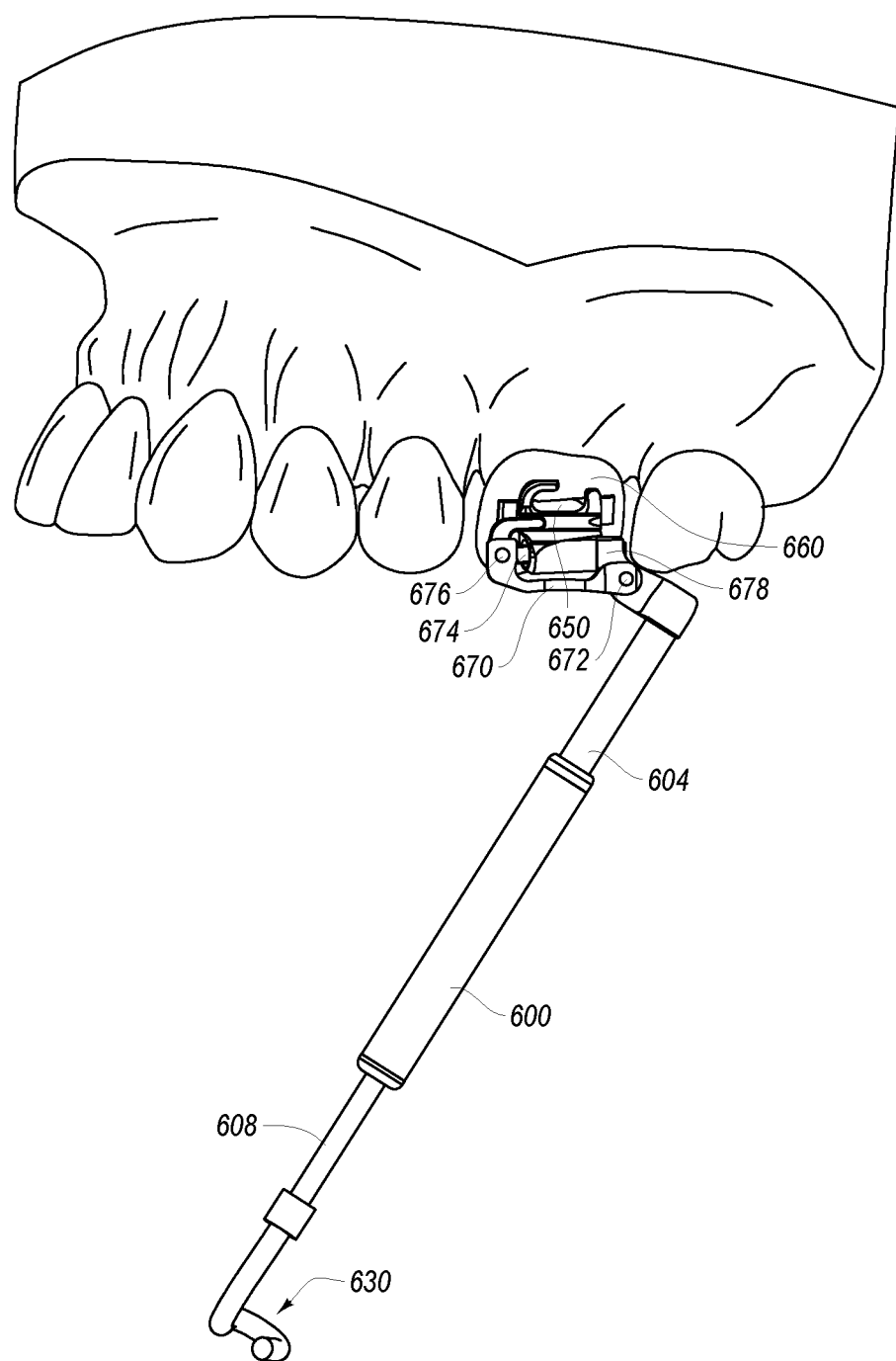

FIGS. 6B-6D illustrate the latch mechanism being used to selectively lock force module or assembly 600 to buccal tube 650 attached to a tooth 660. As illustrated in FIG. 6B, a distal end of pivot pin 674 is positioned near a proximal opening or passageway 652 through a tube 654 of buccal tube 650. First pivot connection or structure 672 and/or second pivot connection or structure 676 permit force module or assembly 600 to be placed in a desired configuration relative to the latch mechanism during the installation process. As illustrated in FIG. 6C, the distal end of pivot pin 674 is inserted through and emerges beyond tube 654. Thereafter, second pivot connection or structure 676 permits body 670 of the latch mechanism to be rotated toward pivot pin 674 in order for latch member 678 to be brought closer to the distal end of pivot pin 674. As illustrated in FIG. 6D, further rotation of body 670 toward pivot pin 674 brings latch member 678 into locked engagement with the distal end of pivot pin 674. Once force module or assembly 600 has been attached to buccal tube 650, it may be attached to a tooth on an opposing jaw side by means of hook 630 at the proximal end of push rod 608.

As illustrated in FIG. 6B, buccal tube 650 can include an auxiliary hook 656 and latch mechanism can also include an auxiliary hook 680 for attachment of elastic members as desired to effect a desired orthodontic treatment.

Figure 7A:
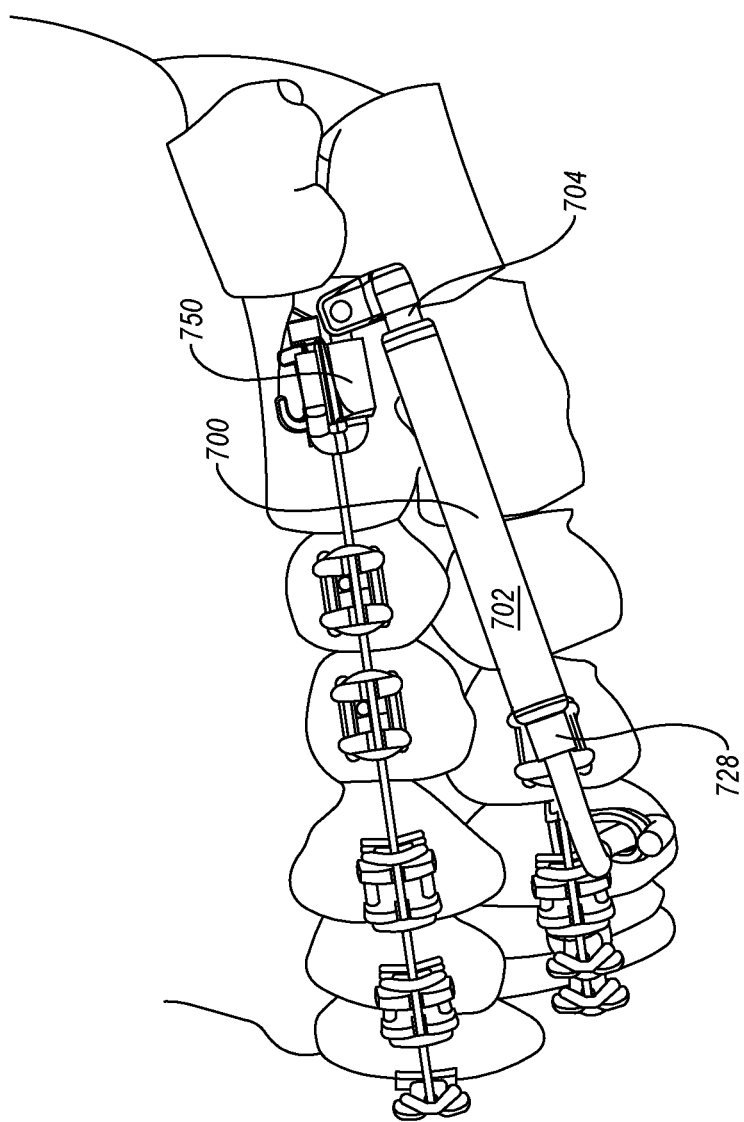
FIGS. 7A and 7B are perspective views of a patient's upper and lower jaws in which a force module or force module assembly as disclosed herein has been installed between the upper and lower jaws to correct a class II malocclusion.
Figure 7B:
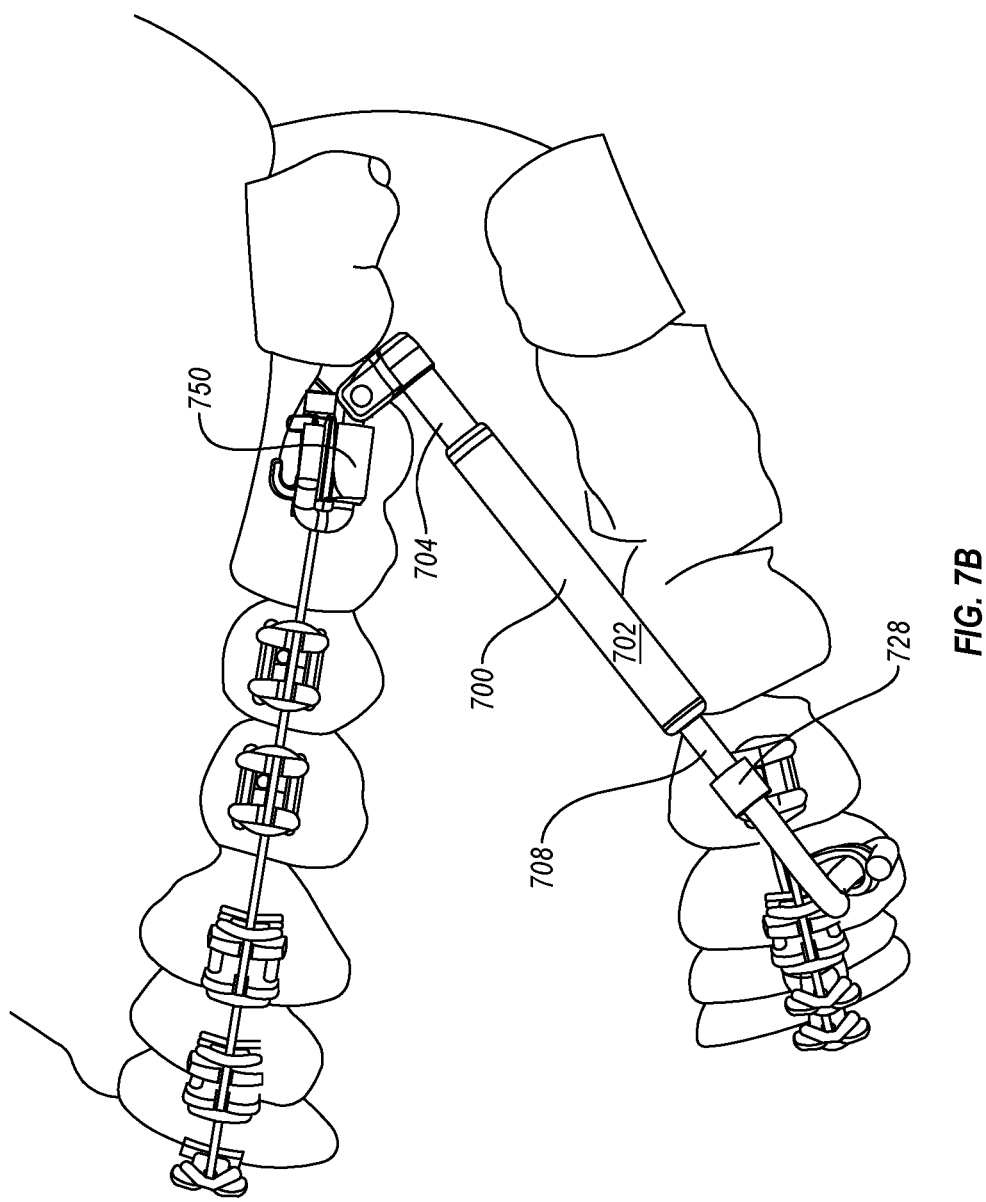

FIGS. 7A and 7B illustrate an orthodontic force module or force module assembly 700 as disclosed herein attached between a patient's upper and lower jaws to correct a class II malocclusion. A distal end of force module or assembly 700 is attached to a buccal tube 750 on a posterior tooth (e.g., molar) of a patient's upper jaw. A proximal end of force module or assembly 700 is attached to a bracket or archwire on an anterior tooth (e.g., canine) of a patient's lower jaw.

FIG. 7A illustrates the configuration of force module or assembly 700 when the patient's jaws are fully closed, wherein force module or assembly 700 is at maximum compression. In this configuration, collar 728 bears against outer body 702 and plunger 704 is advanced proximally within outer body. This causes a compressible spring (not shown) within outer body 702 of force module or assembly 700 to exert a force that urges the teeth of the upper jaw and/or lower jaw of the patient to move relative to each other in order to correct a Class II malocclusion. In this example, force module or assembly 700 exerts a force that corrects an overjet of the upper jaw relative to the lower jaw.

FIG. 7B illustrates the configuration of force module or assembly 700 when the patient's jaws are in an open position. In this configuration of force module or assembly 700, push rod 708 is in an extended position such that collar 728 of push rod 708 does not bear against the proximal end of outer body 702. In this configuration, the compressible spring within outer body 702 of force module or assembly 700 does not exert a force to the dental arches of the upper jaw and/or lower jaw of the patient. Corrective forces progressively exerted on the upper and lower jaw as the patient brings the upper and lower jaws together.

IV. Exemplary L-Shaped Connector Pin for Selective Attachment and Release of an Orthodontic Force Module to a Buccal Tube Another embodiment of the present disclosure is directed to connectors for coupling an orthodontic force module to a buccal tube portion of a molar bracket. The connector includes a generally L-shaped connector body including a buccal tube coupling leg forming a long leg of the L, while a force module coupling leg forms a shorter leg of the L. The buccal tube coupling leg extends from a distal end towards a free proximal end. It is the free proximal end that is inserted into a buccal tube of a molar bracket during use. The force module coupling leg is rigidly attached to the distal end of the buccal tube coupling leg. The free proximal end of the buccal tube coupling leg can be split or otherwise compressible, and also includes an enlarged locking protrusion so as to lock the buccal tube coupling leg within the buccal tube once the leg is fully inserted into a corresponding buccal tube. The shaft of the force module coupling leg is sized so as to be insertable through a hole formed through a flange near a distal end of the force module, and may include an enlarged head at its free end opposite the attachment end, which prevents the force module from sliding off of the force module coupling leg. When the force module coupling leg includes an enlarged head, the attachment end of the force module coupling leg may be inserted through the force module flange hole prior to attachment of the force module coupling leg to the buccal tube coupling leg, after which the two legs are rigidly attached (e.g., by laser welding) together.

FIGS. 8-11 illustrate an alternative L-shaped connector that may be used to attach an end of a force module or assembly to an orthodontic buccal tube.

Figure 8:
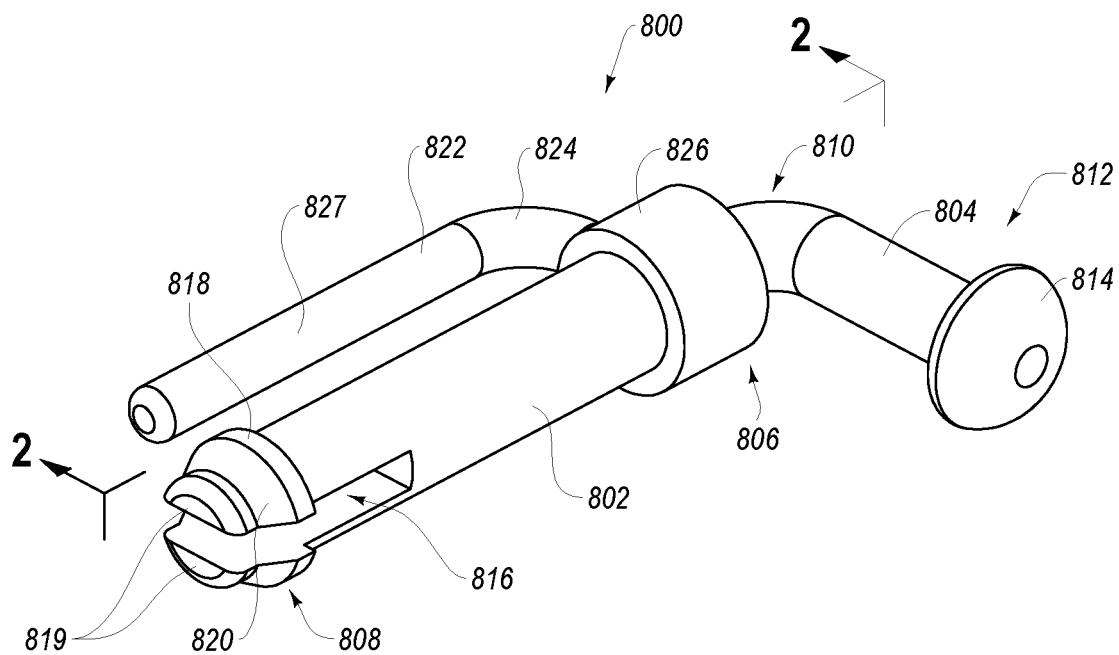
FIG. 8 is a perspective view of another pin that may be used to attach an end of a force module or assembly to an orthodontic buccal tube, where the pin is L-shaped.
Figure 9:
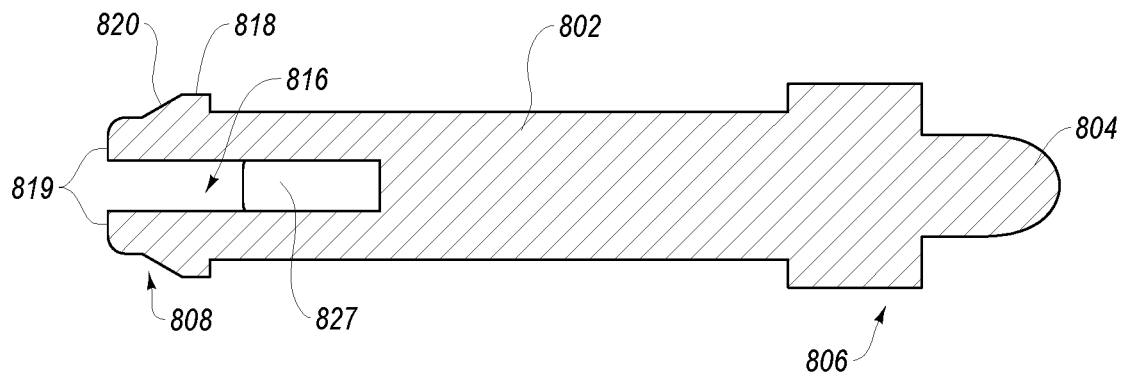
FIG. 9 is a cross-sectional view of the L-shaped connector pin of FIG. 8.

FIGS. 8-9 show an exemplary L-shaped connector 800. Connector 800 includes a buccal tube coupling leg 802 and a force module coupling leg 804. Buccal tube coupling leg 802 extends longitudinally from distal end 806 towards a free proximal end 808. A first end 810 of force module coupling leg 804 is attached (e.g., by welding) to distal end 806 of buccal tube coupling leg 802. An opposite free end 812 of force module coupling leg 804 includes an enlarged head 814 that is diametrically larger than the shaft of leg 804. Buccal tube coupling leg 802 further includes a split 816 at its free proximal end 808, as well as an enlarged locking protrusion 818, also at proximal end 808. Locking protrusion 818 is diametrically enlarged relative to the shaft of leg 802. As shown, split 816 comprises a recess or to void extending from free proximal end 808 distally past locking protrusion 818, partially into the shaft of leg 802.

In one embodiment, the split 816 may be centered relative to leg 802 so as to be disposed along a central longitudinal axis of leg 802. Alternatively, the split may not be centered, but be offset. As shown, split 816 may extend lingually-labially through leg 802. Alternatively, the split may extend gingivally-occlusally. The split 816 may extend over a length that is between about 10 percent and about 50 percent of the total length of leg 802. In another embodiment, the length of split 816 may be between about 20 percent and about 40 percent of the total length of leg 802. In any case, the split is sufficiently long so as to extend into the shaft of leg 802 at least as far as the location of locking protrusion 818. Preferably, the split extends beyond the location of locking protrusion 818, as this allows the locking protrusion 818 to be more easily compressed so as to fit through the buccal tube of a molar bracket.

As shown, a nose 819 at the free end 808 of leg 802 may be of a diameter that is smaller than that of the remaining shaft portion of leg 802. In addition, leading edge 820 of locking protrusion 818 may be tapered so as to be thinnest adjacent nose 819 and thicken towards the opposite end. Such a nose 819 aids in guiding the proximal end 808 into the buccal tube, while tapering of the leading edge 820 provides for easier progressive insertion of leg 802 into the buccal tube. As the leading edge 820 is progressively pressed into the distal end of the buccal tube, split 816 will allow the portion of leg 802 adjacent leading edge 820 and protrusion 818 to compress, allowing the locking protrusion 818 to pass through a passageway in the buccal tube.

A large diameter stop 826 that is enlarged relative to the shaft of leg 802 may be provided at distal end 806 so as to act as a stop against over insertion of leg 802 into the buccal tube. For example, stop 826 may have a diameter that is larger than the inside tube diameter of the buccal tube so that stop 826 cannot be inserted into the buccal tube passageway. The distance between protrusion 818 and stop 826 may be equal to or only slightly longer than the length of the buccal tube, so that the central portion of the shaft of leg 802 is received within the buccal tube, while locking protrusion 818 extends from the proximal or mesial end of the buccal tube and contacts the proximal end of the buccal tube, and stop 826 is disposed against the distal end of the buccal tube.

As shown in FIG. 8, an anti-rotation stop 822 may be attached to distal end 806 of leg 802. Stop 822 may also be L-shaped, including an attachment leg 824 that rigidly attaches stop 822 to distal end 806, as well as a buccal tube contacting leg 827 having a free end. As shown, leg 827 may be longer than attachment leg 824. As shown, leg 827 of stop 822 may extend generally parallel and in the same direction as buccal tube coupling leg 802 although other angles or shapes are possible.

Although illustrated as being generally round in cross-section, it will be understood that at least some of the components may have cross-sections that are other than round (e.g., oval, square, rectangular, etc.). As seen in FIG. 8, the components may have different thicknesses or diameters relative to one another. For example, the buccal tube coupling leg 802 may have a larger diameter than both force module coupling leg 804 and anti-rotation stop 822, while leg 804 may be somewhat larger in diameter than stop 822.

The connector 800 may be assembled from multiple pieces. For example, legs 802, 804, and stop 822 may be separate from one another initially. During manufacture, end 810 of leg 804 may be attached to distal end 806 of leg 802 by welding (e.g., laser welding), soldering, brazing, an adhesive, or any other suitable attachment technique. Similarly, leg 824 of stop 822 may be laser welded or otherwise attached to distal end 806. Prior to attaching end 810 to distal end 806, end 810 may be inserted through a passageway in a flange of the force module, so that the force module becomes permanently and non-releasably coupled to leg 804. In such an embodiment, the flange of the force module is trapped between enlarged head 814 on one end and the large diameter stop 826 of leg 802 on the other end (see FIG. 10A).

Figure 10A:
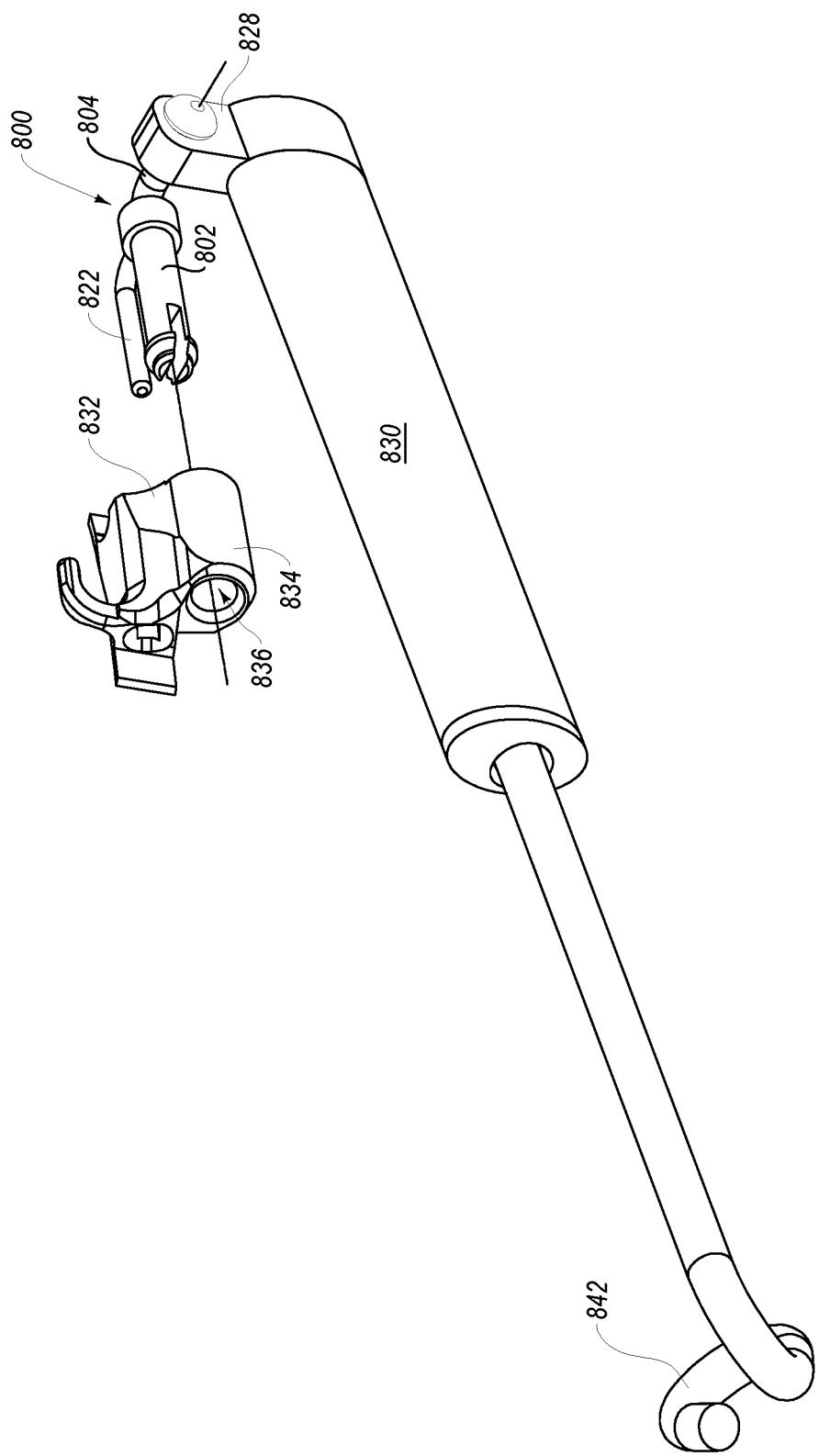
FIG. 10A is a perspective view of the L-shaped connector, a molar bracket, and a force module before the L-pin connector is coupled to the molar bracket.
Figure 10B:
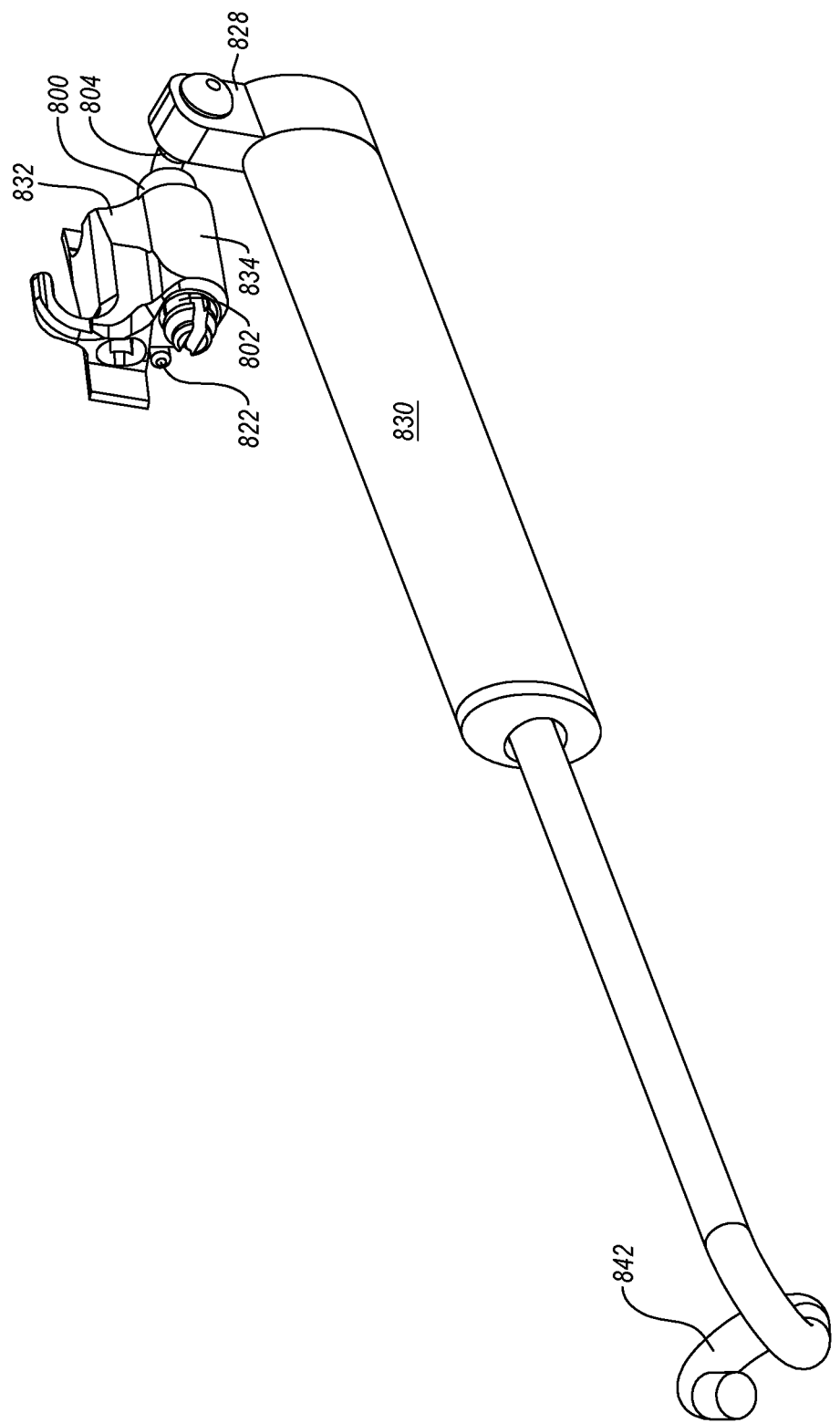
FIG. 10B is a perspective view of the L-shaped connector, molar bracket, and force module of FIG. 10A once the buccal tube coupling leg of the L-shaped connector has been inserted into the molar bracket so that the L-shaped connector couples the distal end of the force module with the molar bracket.

FIG. 10A illustrates a separate molar bracket 832 and the L-shaped connector 800 where connector 800 is shown coupled to a flange 828 of a force module 830 (e.g., which coupling may be accomplished as described above during manufacture of connector 800). Molar bracket 832 includes a buccal tube 834 having an attachment through-hole 836. FIG. 10B shows the proximal end of leg 802 having been inserted within through-hole 836 of buccal tube 834, coupling connector 800 to buccal tube 834.

Once coupled as shown in FIG. 10B, connector 800 is coupled to buccal tube 834 by a pin-hinge mechanism which allows rotation of connector 800 about leg 802 within buccal tube 834. Such rotation is in an in-out (i.e., labial-lingual) direction relative to the tooth surface. Similarly, connector 800 is coupled to force module 830 by a pin-hinge mechanism which allows rotation of force module 830 about leg 804 rotatably connected to flange 828. Such rotation is in an up-down (i.e., occlusal-gingival) direction relative to the tooth surface.

Figure 11:
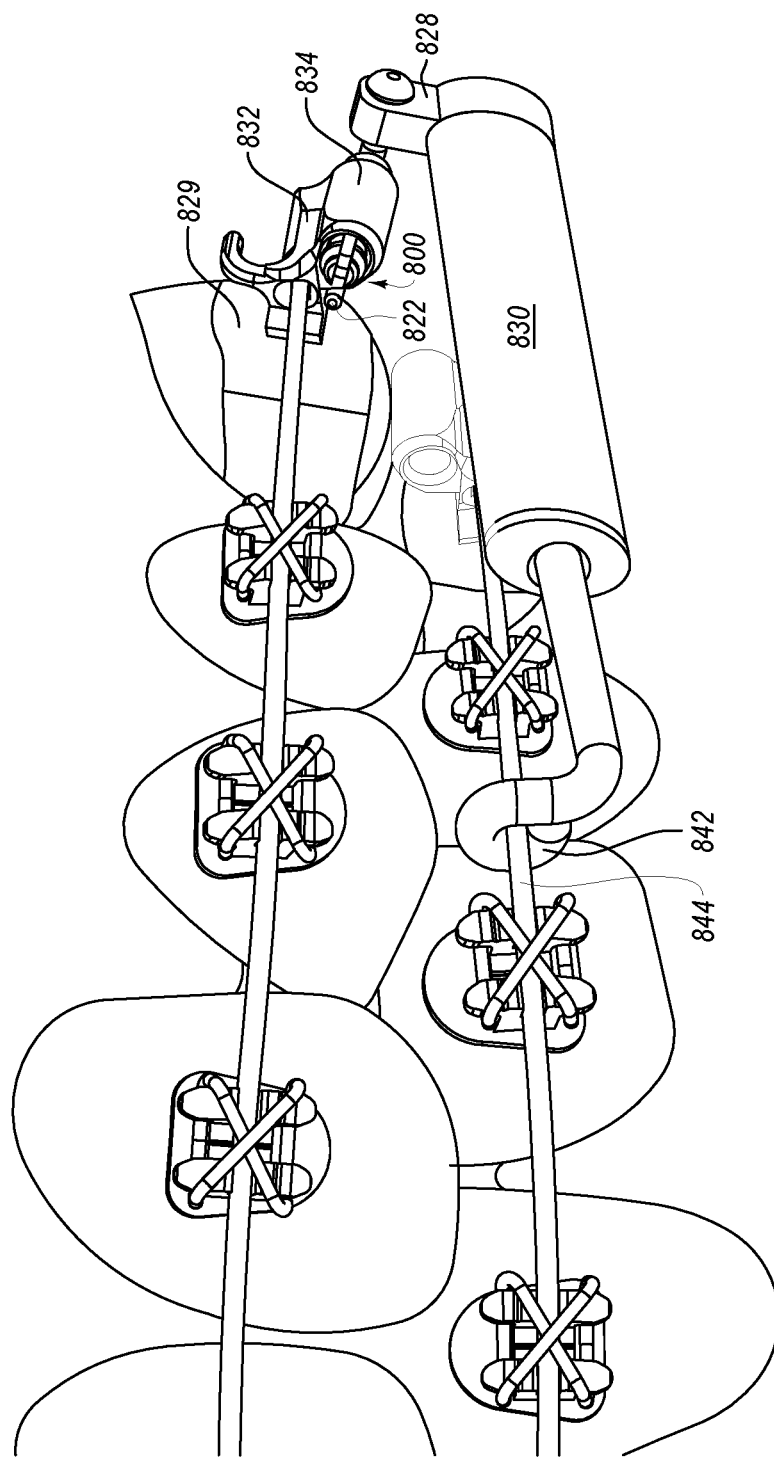
FIG. 11 is a perspective view of the force module coupled with the molar bracket by means of the L-shaped connector with all components installed in a patient's mouth.

As shown in FIG. 11, the force module 830 and molar bracket 832 are securely and indirectly coupled to one another, but the connector 800 permits sufficient freedom of movement between the molar bracket 832 (affixed to a molar 829 of the upper jaw) and the force module 830 (coupled at its proximal end by hook 842 to a bracket or arch wire 844 of the lower jaw) when the patient opens/closes his or her mouth. The coupling is indirect in that the force module 830 is not directly coupled to the molar bracket 832, but through the connector 800 which acts as an interface between the force module 830 and molar bracket 832. The coupling mechanism allows the connector 800 to rotate inwardly and outwardly about buccal tube coupling leg 802, and also allows the force module 830 to rotate upwardly and downwardly about force module coupling leg 804.

The coupling is dynamic in that it allows the patient to open and close his or her mouth while the various components involved within the coupling (e.g., buccal tube 834, connector 800, flange 828) are allowed to adjust, rotate, and move relative to one another as necessitated by the patient's jaw movements as a result of pin hinges 802 and 804. The proximal end of force module 830 is coupled to the arch wire 844 of the lower dental arch through hook 842. Although hook 842 is illustrated as coupled to lower arch wire 844, it will be understood that any suitable or known coupling mechanism may be used for coupling the proximal end of the force module 830 to the lower arch wire 844 or bracket of the lower dental arch.

The illustrated configuration is for class II correction. However, correction of a class III malocclusion may be accomplished by opposite attachment of a force module. In other words, proximal hook 842 may be connected to the arch wire or bracket near the patient's canine of the upper jaw, while flange 828 at the distal end of the force module is coupled to a connector 800, which is in turn coupled to a buccal tube 834 of a molar bracket 832 affixed to the patient's molar of the lower dental arch. It will also be understood that orthodontic force modules other than those described herein may be connected to a buccal tube bracket by the L-shaped connector (or any of the other connectors disclosed herein).

L-shaped connector 800 may be formed of any suitable material. Exemplary materials include metal or plastic. Exemplary metal materials include stainless steel, titanium alloys (e.g., nickel-titanium), and/or a cobalt-chromium alloy. Various exemplary stainless steels include ANSI 17-4, ANSI 400 series stainless steels, and/or ANSI 300 series stainless steels (e.g., ANSI 303, ANSI 304, and/or ANSI 316). The connector and its components may be formed by machining, metal injection molding, casting, drawing, or any other suitable technique. Machining the connector from metal may be particularly preferred as compared to metal injection molding as the strength is significantly greater when forming any given component by machining as compared to metal injection molding where all other parameters are equal (e.g., same part thickness, geometry, etc.). In another embodiment, the connector may be formed of a suitable high strength, relatively rigid plastic, such as polycarbonate, nylon, and/or Delrin, any of which may be glass loaded for reinforcement.

V. Additional Exemplary Connector Assemblies for Selective Attachment and Release of an Orthodontic Force Module to a Buccal Tube Another embodiment of the present disclosure is directed to alternative connectors and connector assemblies for coupling an orthodontic force module to a buccal tube portion of a molar bracket. The connector assembly comprises a connector body, a first coupling pin for coupling a buccal tube of a molar bracket to the connector body, and a second coupling pin for coupling a flange of an orthodontic force module to the connector body. The connector body includes a body, a buccal tube receiving recess formed into a gingival side of the body for receiving a buccal tube of a molar bracket, and a flange receiving recess formed into an opposite side of the body for receiving a flange disposed at or near a distal end of the force module. The body further includes a first channel disposed through the body that is axially aligned with the buccal tube receiving recess, and a second channel disposed through the body that is axially aligned with the flange receiving recess. In use, the first coupling pin is inserted through the first channel and the buccal tube, coupling the buccal tube to the connector body. The second coupling pin is similarly inserted through the second channel and a hole formed through the flange of the force module, coupling the flange of the force module to the connector body.

The connector assemblies may be formed of any suitable material, such as metal (e.g., stainless steel), plastic, or an elastomeric material (e.g., silicone). In any case, the assembly provides a dynamic but secure coupling mechanism between the force module and the molar bracket affixed to the patient's molar. Advantageously, the coupling mechanism allows the connector body to spontaneously adjust its orientation and spatial relationship relative to the molar bracket on one side and the force module on the other side as needed (e.g., as the upper and lower jaws are moved relative to one another). In this way, the patient is able to continue with normal activities while the orthodontic force module remains indirectly coupled to the molar bracket through the connector assembly.

Figure 12:
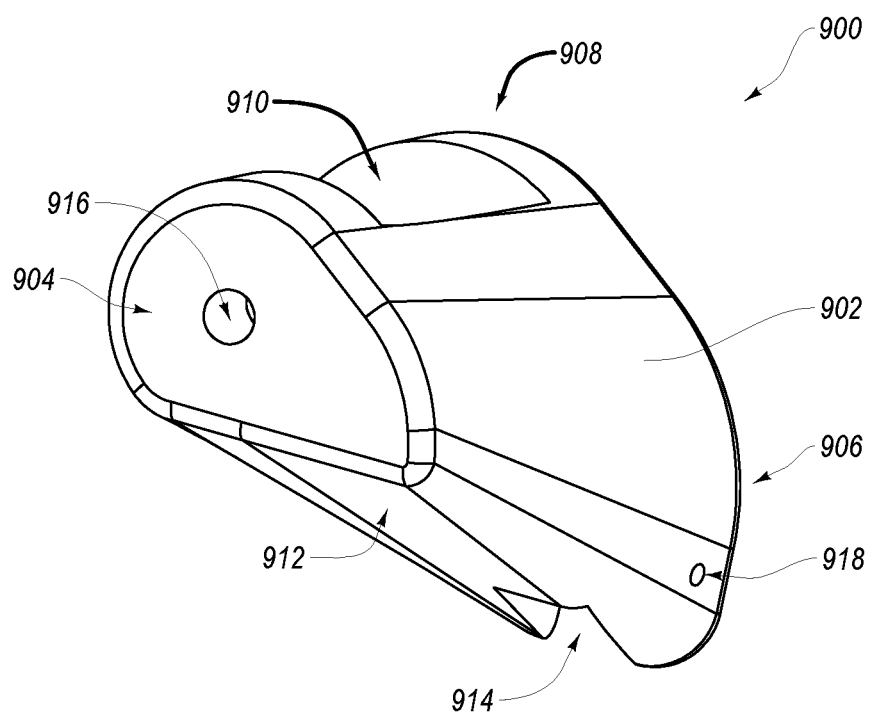
FIG. 12 is a perspective view of another connector that may be used to attach an end of a force module or assembly to an orthodontic buccal tube, where the connector comprises an elastomeric connector body.
Figure 13:
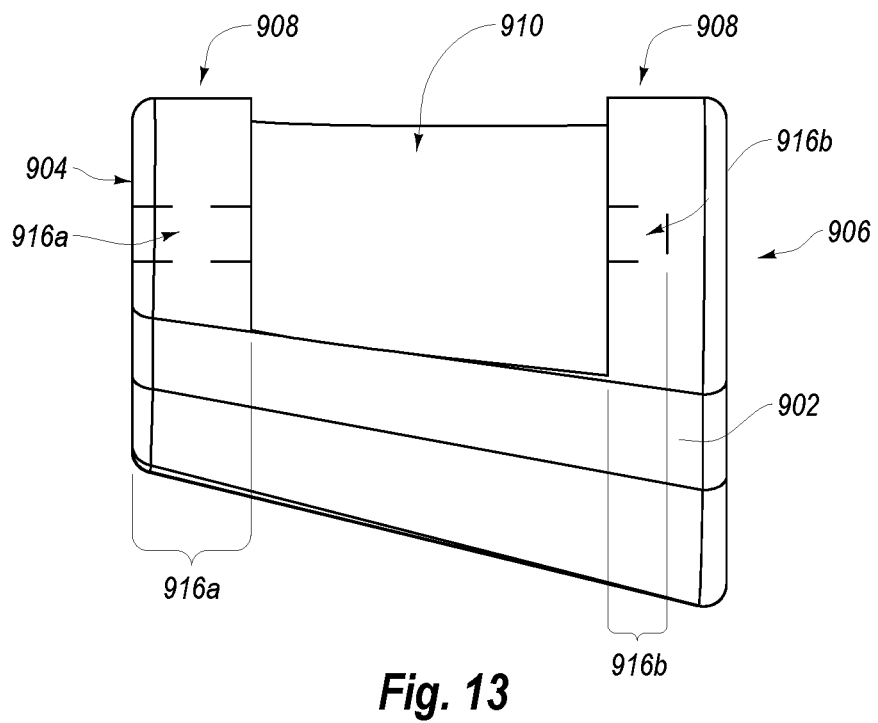
FIG. 13 is a gingival top view of the connector body of FIG. 12.
Figure 14:
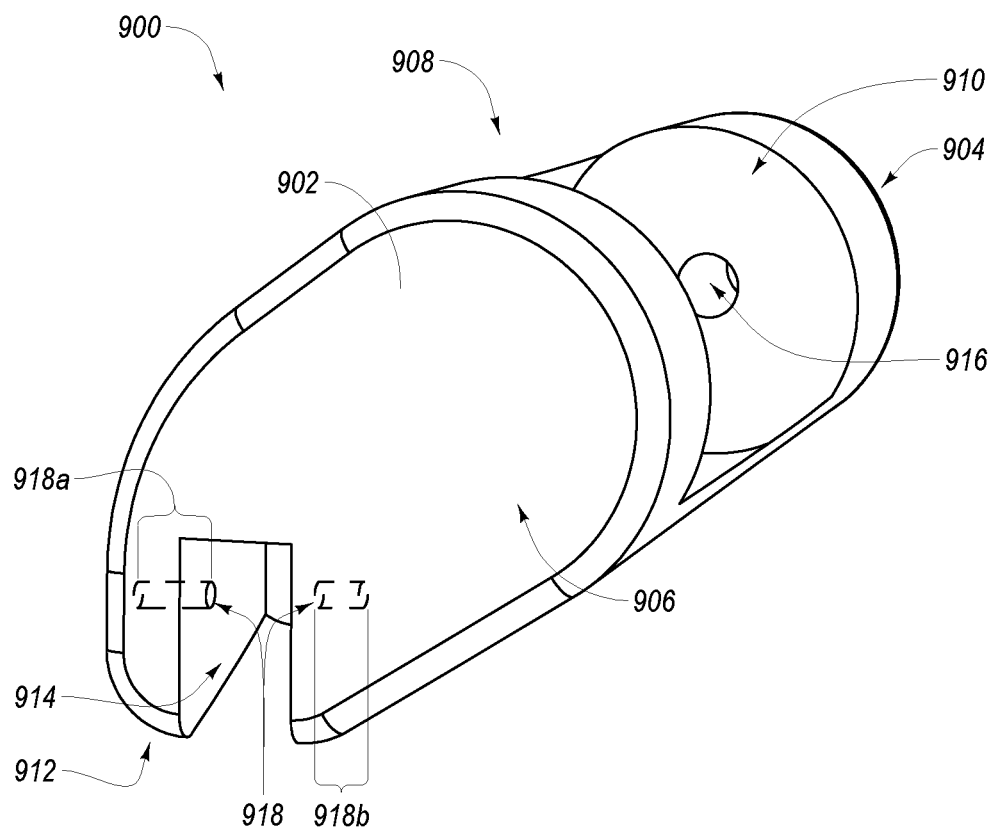
FIG. 14 is another perspective view showing the distal end of the connector body of FIG. 12.

FIGS. 12-13 show an exemplary connector 900 including a body 902 having mesial and distal ends 904 and 906, respectively. A buccal tube receiving recess 910 is formed into the gingival side 908 of body 902. As perhaps best seen in FIG. 14, recess 910 may also extend to the lingual or "back" side of body 902 as well to facilitate insertion of a buccal tube of a molar bracket into recess 910. Occlusal side 912 includes a flange receiving recess 914 formed therein for receiving a flange at or near the distal end of a force module. Body 902 further includes a first channel 916 that is axially aligned with recess 910 so that a coupling pin inserted into channel 916 passes through mesial portion 916a (FIG. 13), through the buccal tube, and then into distal portion 916b (FIG. 13), coupling the buccal tube with body 902. This coupled configuration is perhaps most clearly shown in FIG. 15B.

Body 902 also includes a second channel 918 that is axially aligned with flange receiving recess 914 so that a second coupling pin inserted into channel 918 passes through labial portion 918a (FIG. 14), through the flange, and then into lingual portion 918b (FIG. 14), coupling the force module flange to the connector 900.

Figure 15A:
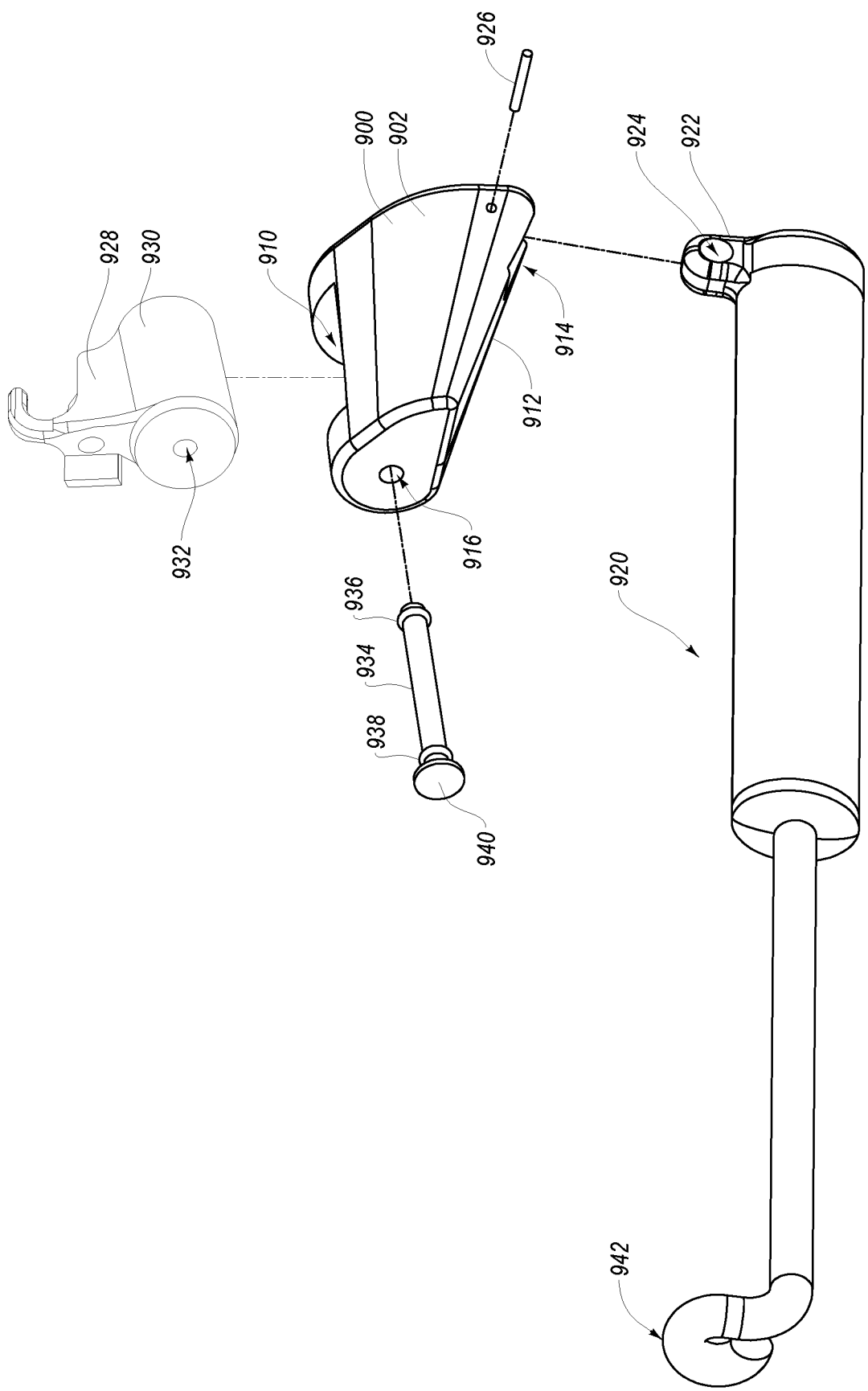
FIG. 15A is an exploded view of an exemplary connector assembly including the connector body of FIG. 12, a first coupling pin, and a second coupling pin.

FIG. 15A shows in exploded view to better understand how the various components are coupled to one another. Force module 920 includes a flange 922 disposed near its distal end. Flange 922 includes a through-hole 924 that is transverse to the longitudinal axis of module 920. Flange receiving recess 914 is sized and configured to receive flange 922 therein, so that channel 918 is axially aligned with through-hole 924 when flange 924 is fully seated within recess 918. Second coupling pin 926 is sized and configured to be inserted into channel 918, passing through both portions of channel 918 so that through-hole 924 is disposed between the labial and lingual portions of channel 918. As a result, flange 922 of force module 920 can be coupled to connector body 900 by coupling pin 926. Coupling pin 926 may comprise a simple cylindrical shaft, as shown. Alternatively, pin 926 may include an enlarged proximal head, an L-shaped proximal head, and/or any features described below with respect to first coupling pin 934.

Molar bracket 928 includes a buccal tube 930 for coupling to auxiliary devices, such as a force module. Buccal tube 930 includes a through-hole 932. Buccal tube receiving recess 910 is sized and configured to receive buccal tube 930 therein, so that channel 916 is axially aligned with through-hole 932 when buccal tube 930 is fully seated within recess 910. First coupling pin 934 is sized and configured to be inserted into channel 916, passing through mesial portion 916a, through-hole 932 of buccal tube 930, and then into distal portion 916b. As a result, buccal tube 930 of molar bracket 928 can be coupled to connector 900 by coupling pin 934.

Once coupled, connector 900 is coupled to buccal tube 930 by a pin-hinge mechanism which allows in-out type rotation of body 902 about pin 934. Similarly, connector 900 is coupled to force module 920 by a pin-hinge mechanism which allows up-down type rotation of force module 920 about pin 926. In this way, the force module and molar bracket are securely and indirectly coupled to one another, but the connector body still permits sufficient freedom of movement as the molar bracket 928 (affixed to a molar of the upper jaw) moves relative to the force module 920 (coupled at its proximal end 942 to a bracket or arch wire of the lower jaw). The coupling is indirect in that the force module 920 is not directly coupled to the molar bracket 928, but through the connector 900 which acts as an interface between the force module 920 and molar bracket 928. The coupling mechanism allows the connector 900 to rotate inwardly and outwardly about first coupling pin 934, and also allows the force module 920 to rotate upwardly and downwardly about second coupling pin 926.

Figure 15B:
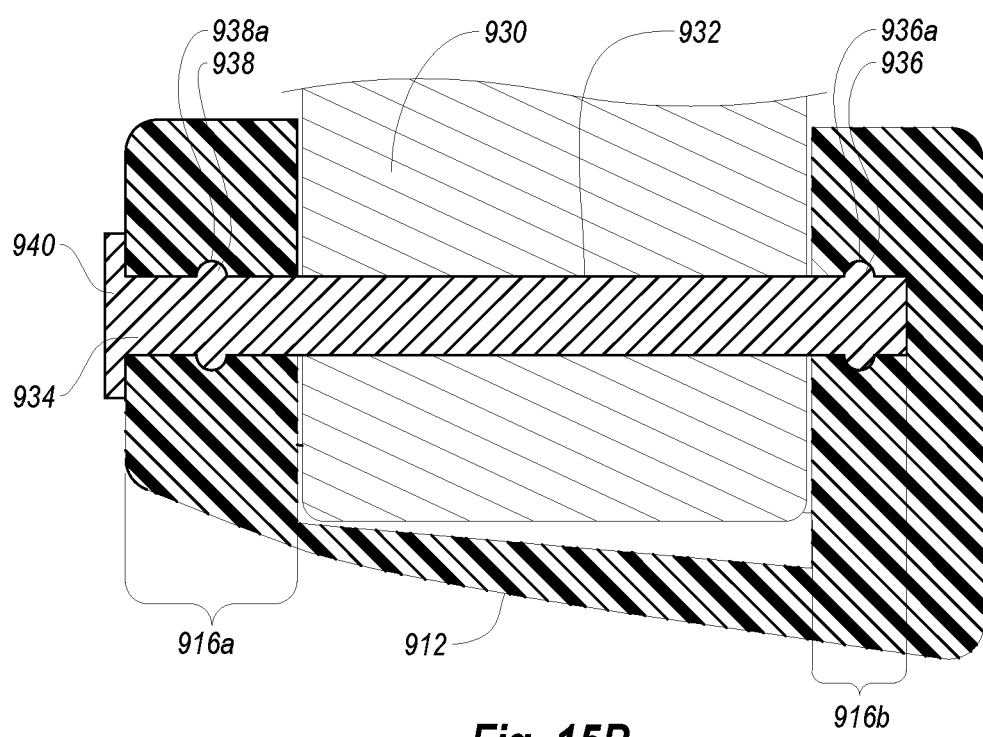
FIG. 15B is a cross-sectional view through the connector body of FIG. 12 showing the first coupling pin inserted into a corresponding first channel of the connector body and the buccal tube of a molar bracket so as to couple the connector body to the buccal tube.

FIG. 15B illustrates coupling pin 934 inserted into channel 916, passing through mesial portion 916a, through hole 932 of buccal tube 930, and into distal portion 916b of channel 916. Coupling pin 934 is illustrated as including an enlarged proximal head 940 that is larger than the shaft of pin 934. Of course, pin 934 may be differently configured (e.g., with an L-shaped bend at its proximal head, or with no enlarged head at all). Coupling pin 934 may also include annular protrusions 936, 938 for engagement with corresponding annular recesses 936a, 938a that are sized, shaped, and positioned within channel 916 so as to receive a corresponding protrusion.

Although connector body 900 may be formed of any suitable material (e.g., metal, plastic, an elastomeric material, or even ceramic), in one embodiment manufacture from an elastomeric material (e.g., silicone) is preferred. Such a material exhibits substantial elasticity (e.g., at least about 50% elongation). In such an embodiment, coupling pin 934 (as well as coupling pin 926) may be formed of metal or relatively rigid plastic and the elastic nature of body 900 allows body 900 to elastically flex, bend, and compress so as to allow entry of enlarged protrusions 936, 938 into channel 916. As seen in FIG. 15B, channel 916 may be smaller diametrically than protrusions 936, 938. Elastic body 900 is able to elastically compress and adapt around protrusions 936, 938 as coupling pin 934 is pushed into channel 916, and when protrusions 936, 938 reach recesses 936a, 938a the annular protrusions 936, 938 snap into recesses 936a, 938a respectively, retaining coupling pin 934 in place. Because connector body 900 is elastomeric, coupling pin 934 can be pulled out upon application of sufficient pulling force, but the locking mechanism of protrusions 936, 938 and recesses 936a, 938a will hold the pin 934 in place so as to prevent inadvertent pin removal.

As mentioned, body 900 may be formed of any suitable material. Exemplary metal materials include stainless steel, titanium alloys (e.g., nickel-titanium), and/or a cobalt-chromium alloy. Various exemplary stainless steels include ANSI 17-4, ANSI 400 series stainless steels, and/or ANSI 300 series stainless steels (e.g., ANSI 303, ANSI 304, and/or ANSI 316). Metal connector bodies may be formed by machining, metal injection molding, casting, or any other suitable technique. Coupling pins may similarly be formed by machining, metal injection molding, casting, drawing, or any other suitable technique. When formed of metal, machining may be particularly preferred as strength is significantly greater when forming any given component by machining as compared to metal injection molding where all other parameters are equal (e.g., same part thickness, geometry, etc.). In another embodiment, the connector body and/or the coupling pins may be formed of a suitable high strength relatively rigid plastic, such as polycarbonate, nylon, and/or Delrin, any of which may be glass loaded for reinforcement. In another alternative, the body and/or coupling pins may be formed of ceramic.

Although metals, plastics, or even ceramic materials may be employed, according to one embodiment, the connector body comprises an elastomeric material. Such materials may be thermoset or chemical cure elastomers (e.g., silicone), or thermoplastic elastomers. Exemplary silicone and thermoplastic elastomer materials suitable for use preferably exhibit elastic elongation of at least about 50%, more preferably at least about 75%, even more preferably at least about 100%, and most preferably at least about 300%. Accordingly to one embodiment, the elastic elongation is in a range of about 50% to about 2000%, typically in a range of about 75% to about 1500%, more typically in a range of about 100% to about 1000%, and most typically in a range of about 300% to about 800%.

The employed elastomeric material may include any suitable durometer hardness value. Durometer is a measure of the hardness, or ability of the material to resist permanent indentation. Specific ASTM testing procedures (e.g., ASTM D2240) will be known to those of skill in the art. Typical durometer values may range between a Shore A durometer hardness between about 20 and about 90. The higher the value, the harder the material. Materials exhibiting even higher hardness values (e.g., those measured on the Shore D scale) may also be suitable for use.

Any of various silicone materials may be employed. One exemplary silicone material, KEG2000-50A/B, is available from Shin-Etsu Silicones of America, located in Akron, Ohio. Various other Shin-Etsu silicone products and silicone materials from other suppliers can also be used.

Examples of thermoplastic elastomers that may be used include styrene-ethylene-butylene-styrene (SEBS) and VERSAflex, a proprietary thermoplastic elastomer alloy that exhibits elastic elongation and other properties similar to silicone. VERSAflex is sold by GLS Corporation, based in McHenry, Ill. A suitable example of a SEBS material is SEBS TPE 45A, available from various providers.

Several exemplary VERSAFLEX thermoplastic elastomer materials, including VERSAFLEX CL30 and VERSAFLEX CL40, are available from GLS Corporation, located in McHenry, Ill. Various other VERSAFLEX products from GLS Corporation can also be used.

Examples of additional elastomeric silicone and silicone-like thermoplastic elastomer materials that may be suitable for use are listed in Table 1 below.

TABLE 1

| Manufacturer | Product | Product Type | Hardness (A) | % Elongation |
|---|---|---|---|---|
| Shin-Etsu | SVX-19550C-7 | Silicone | 50 | 640 |
| Wittenburg B.V. | MT 970 | SEBS | 70 | |
| Wittenburg B.V. | Cawiton PR 2677F | SEBS | 25 | |
| Teknor Apex | MP 1870-1000 | SEBS-TPE | 70 | 600 |
| Bayer | Texin 985 | TPE (Polyether) | 86 | 500 |
| Bayer | Texin 285 Natural | TPE (Polyether) | 85 | 500 |
| Bayer | Texin 1201 | TPE | 67 | 300 |
| GLS Corp. | Versaflex-CL 30 | TPE | 30 | 780 |
| GLS Corp. | Versaflex-CL 40 | TPE | 43 | 690 |
| GLS Corp. | Versaflex 2250 | TPE | 50 | 760 |
| GLS Corp. | Versalloy 9055X-1 | TPE | 53 | 590 |
| GLS Corp. | Dynaflex G2701-1000-02 | TPE | 66 | 590 |
| GLS Corp. | Dynaflex G 2703-1000-02 | TPE | 58 | 690 |
| Dow Corning | TPSiV 3010 | TPE | 50 | 470 |
| Dow Corning | TPsiV 3040-55A | TPE | 55 | 450 |
| Dow Corning | LSR C6-550 | Silicone | 55 | 661 |
| Dow Corning | LSR C6-570 | Silicone | 70 | 442 |
| Dow Corning | Silastic Dev SB 2% bleed | Silicone | 50 | 450 |
| JRS | Excelink 1600B | TPE | 56 | 640 |
| PolyOne | Elastamax EG-9065 | TPE | 65 | 420 |
| Advance Polymers | Duragrip DGR 6250 CL | TPE | 50 | 800 |

TABLE 1-continued

| Manufacturer | Product | Product Type | Hardness (A) | % Elongation |
|---|---|---|---|---|
| Elastocon | Elastocon 2840 | TPE | 40 | 580 |
| Elastocon | Elastocon 2855 | TPE | 55 | 660 |
| Kraiburg | Thermolast TF4THT | TPE | 40 | 610 |
| Kraiburg | Thermolast TF5THT | TPE | 50 | 680 |
| Kraiburg | Thermolast TF6THT | TPE | 60 | 710 |
| AT Plastics | Ateva 2810A | EVA-C | 79 | 820 |
| Arkema | Evatane 33-400 | EVA | 55 | 950 |

Figure 16:
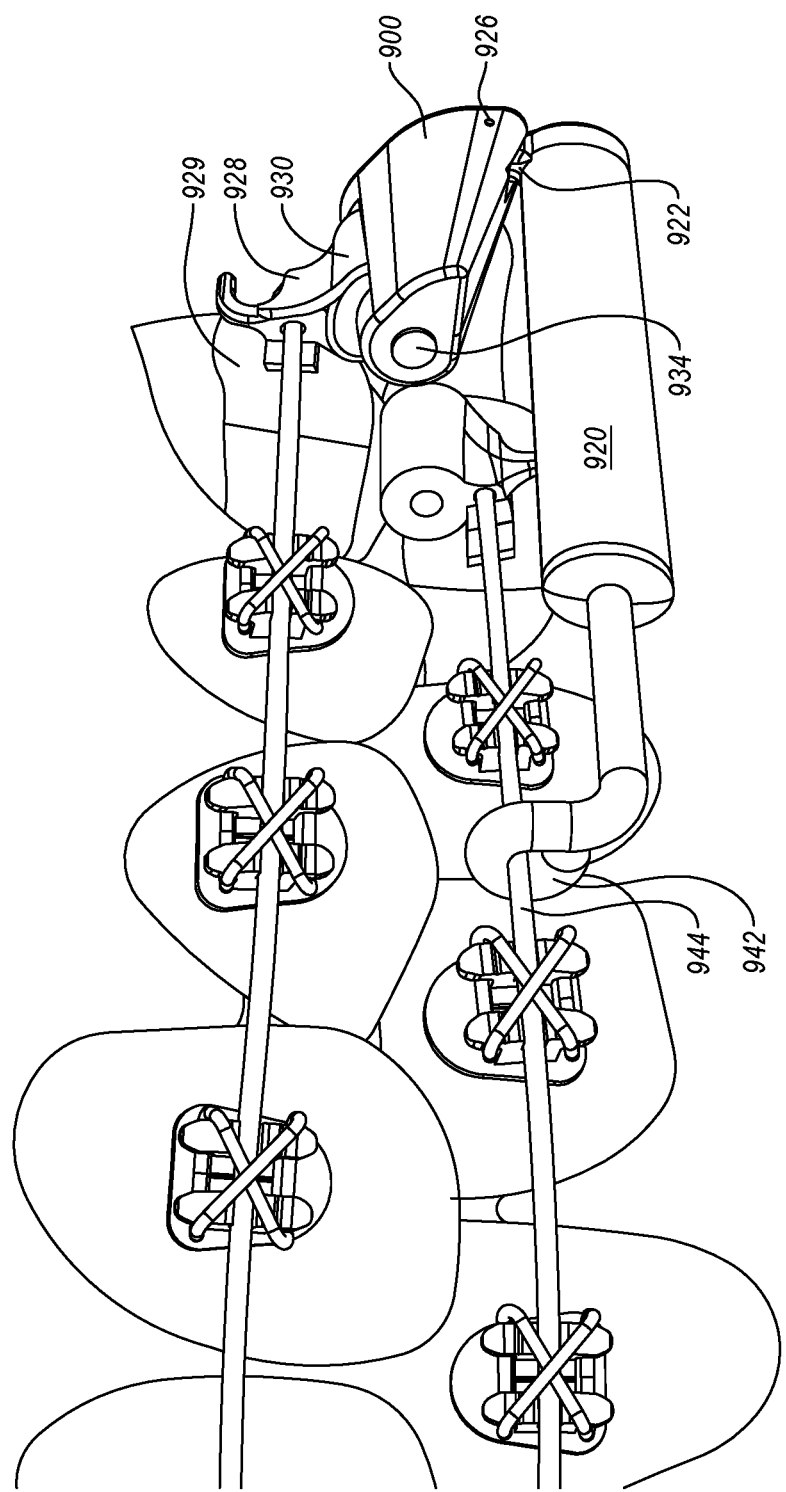
FIG. 16 is a perspective view of the connector assembly of FIG. 15A installed so as to indirectly couple a flange near a distal end of the force module to the buccal tube of the molar bracket secured to the patient's molar.

FIG. 16 illustrates connector 900 installed within a patient's mouth and coupled between buccal tube 930 of molar bracket 928 (which is secured to the patient's upper molar by molar band 929) and flange 922 of force module 920. The coupling is dynamic in that it allows the patient to open and close his or her mouth while the various components involved within the coupling (e.g., buccal tube 930, connector 900, flange 922) are allowed to adjust, rotate, and move relative to one another as necessitated by the patient's jaw movements as a result of pin hinges 934 and 926. The proximal end of force module 920 is coupled to the arch wire 944 of the lower dental arch through hook 942. Although hook 942 is illustrated as coupled to lower arch wire 944, it will be understood that any suitable coupling mechanism may be used for coupling the proximal end of the force module 920 to the lower arch wire 944 or bracket of the lower dental arch. The illustrated configuration is for class II correction. Correction of a class III malocclusion may be accomplished by opposite attachment of a force module. In other words, proximal hook 942 may be connected to the arch wire or bracket near the patient's canine of the upper jaw, while flange 922 at the distal end of the force module is coupled to a connector body, which is in turn coupled to a buccal tube of a molar bracket affixed to the patient's molar of the lower dental arch.

Figure 17:
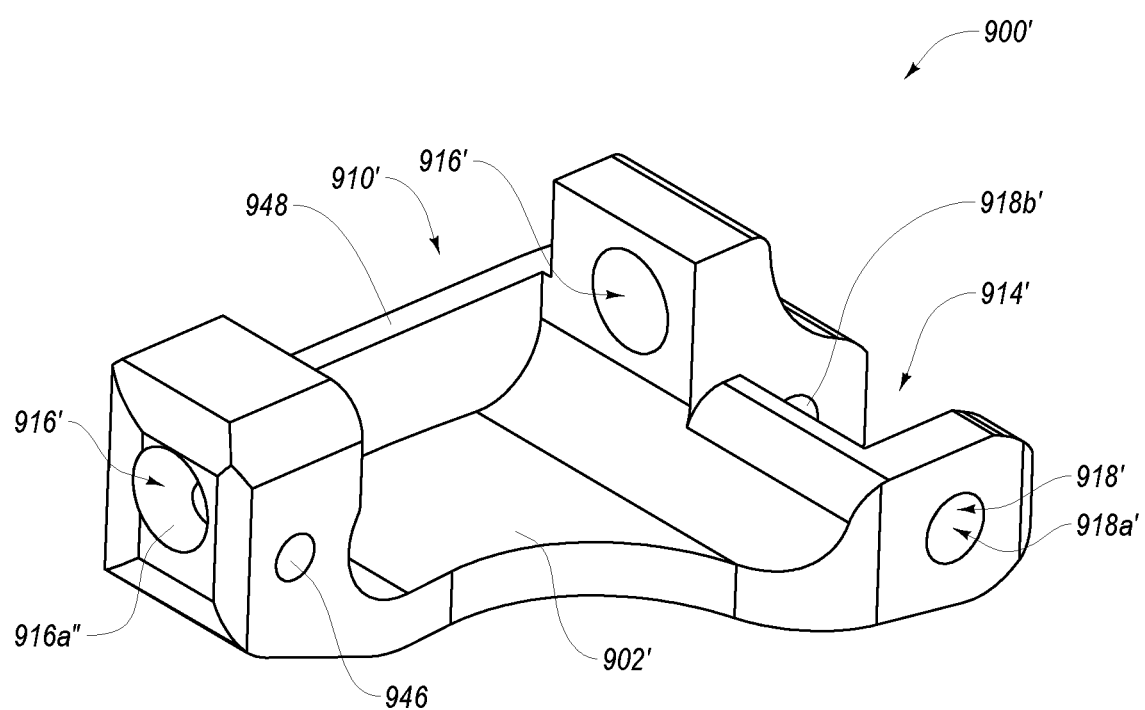
FIG. 17 is a perspective view of another connector that may be used to attach an end of a force module or assembly to an orthodontic buccal tube.
Figure 20:
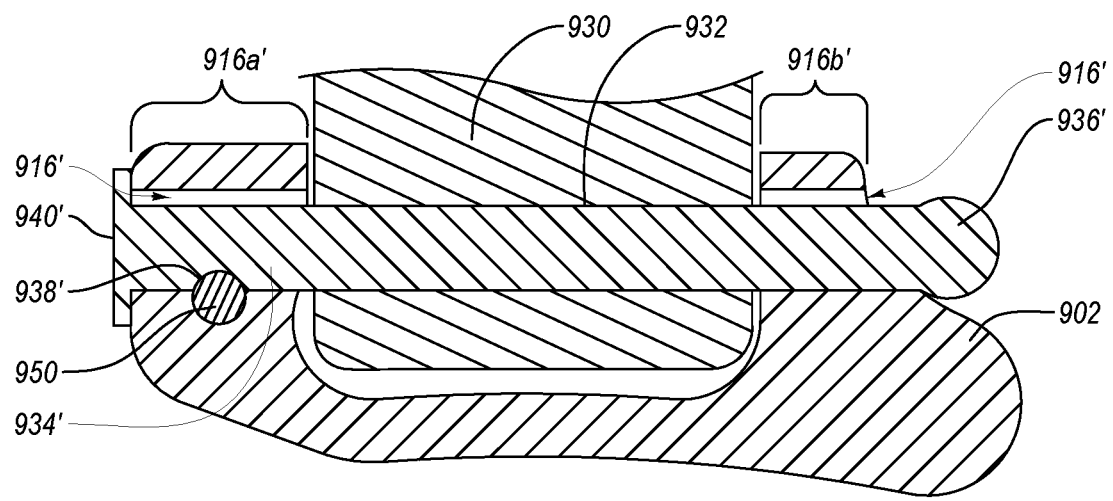
FIG. 20 is a cross-sectional view through the connector body of FIG. 17 showing the first coupling pin inserted into a corresponding first channel of the connector body and the buccal tube of a molar bracket so as to couple the connector body to the buccal tube.

FIG. 17 illustrates an alternative embodiment of a connector 900' including a buccal tube receiving recess 910', a flange receiving recess 914', and a first channel 916' through body 902' that is axially aligned with recess 910' so that during use a coupling pin passes through mesial portion 916a' (FIG. 20), through a buccal tube within recess 910', and then into distal portion 916b' (FIG. 20). A second channel 918' is also provided within body 902' that is axially aligned with recess 914' so that during use a second coupling pin passes through labial portion 918a', through a flange received within recess 914', and into lingual portion 918b'. The above features of body 900' are similar to correspondingly numbered features of the embodiment shown in FIG. 12. In addition, connector body 900' includes a third channel 946 configured to receive a corresponding pin that aids in retaining a coupling pin within channel 916'. Another difference is that channel 916' is illustrated as extending completely through body 902' (FIG. 20).

Connector body 900' further includes an anti-rotation stop 948 disposed occlusally below buccal tube receiving recess 910'. Stop 948 may be configured as a wall that extends from the mesial to distal ends of body 900' and gingivally upwards towards a buccal tube received within recess 910' during use so as to contact the buccal tube, preventing excessive rotation of the connector 900' (and coupled force module) away from the teeth, towards the patient's cheek. In other words, stop 948 helps in maintaining the connector 900' and coupled force module in a desired orientation relative to the patient's jaw so as to prevent unwanted excessive outward rotation about the first coupling pin received within channel 916'.

Figure 18:
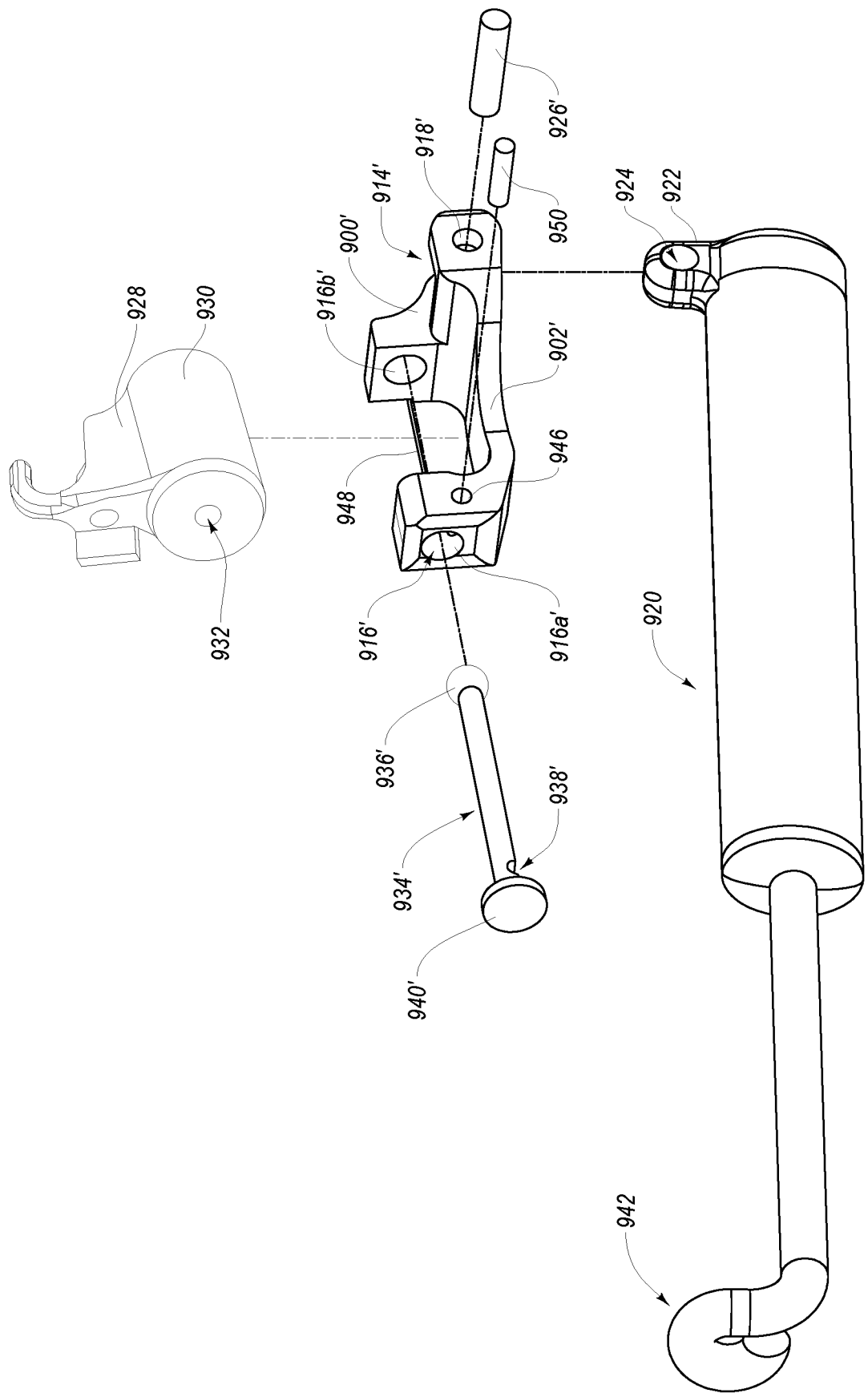
FIG. 18 is an exploded view of an exemplary connector assembly including the connector body of FIG. 17, a first coupling pin, and a second coupling pin.

FIG. 18 is an exploded view showing how the force module and buccal tube are coupled to the connector 900'. The general coupling mechanism is similar to that of FIG. 15A in that coupling pin 934' is inserted into channel 916', with portions 916a' and 916b' sandwiching buccal tube 930 therebetween. Coupling pin 926' is inserted into channel 918' with its labial and lingual portions sandwiching flange 922 therebetween. Coupling pin 934' includes an enlarged proximal head 940', but is somewhat differently configured than coupling pin 934, in that it includes a slightly enlarged or bulbous distal head 936' at the end of the shaft, as well as a recess 938' formed within the pin shaft disposed proximal to bulbous head 936' (e.g., formed into the shaft near proximal head 940'). The shaft of pin 934' may be generally cylindrical or it may include flat surfaces (e.g., having a square or rectangular transverse cross-section), as desired. As perhaps best seen in FIG. 20, bulbous head 936' is sized so as to allow insertion into channel 916 and through hole 932 of buccal tube 930. Once coupling pin 934' is fully inserted, coupling pin 950 is inserted into channel 946. In the fully inserted condition, the recess 938' (e.g., a hemispherical or other concave recess) is aligned with channel 946 so that as pin 950 is inserted into channel 946, it is received into recess 938'. The shaft of pin 934' may be sized smaller relative to channel 916' so as to allow coupling pin 934' to be "lifted" so as to lift recess 938' out of reception with pin 950. In this configuration, the coupling pin 934' may be partially retracted from channel 916 until bulbous head 936' contacts pin 950. Contact between the bulbous head 936' and pin 950 prevents further removal of coupling pin 934' until pin 950 is first removed.

Figure 19:
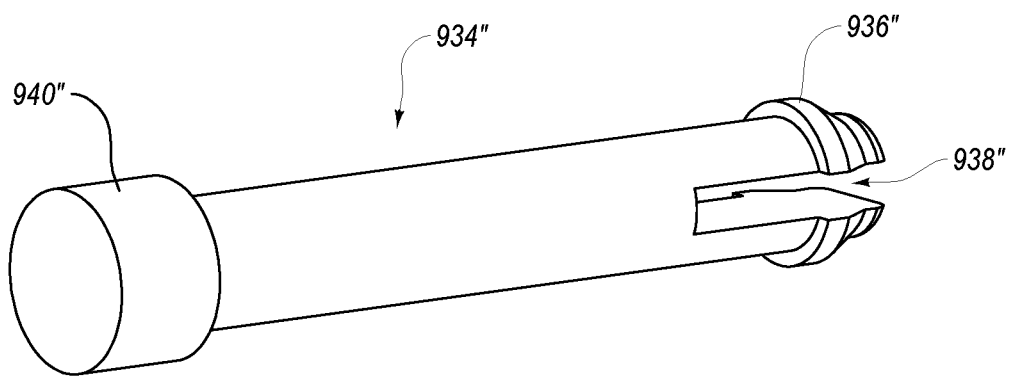
FIG. 19 is a perspective view of an alternative coupling pin.

FIG. 19 illustrates an alternative coupling pin 934" including a split distal end. Split 938" allows the split portion of pin 934" to compress as the pin is inserted through channel 916 or 916' of respective connectors 900, 900'. Pin 934" further includes a locking protrusion 936" at the split distal end of pin 934", which locks the pin 934" in conjunction with enlarged proximal head 940" once pin 934" is fully inserted. For example, the length of the shaft of pin 934" between locking protrusion 936" and enlarged proximal head 940" may be equal to the length of the buccal tube plus channel portions 916a, 916a' and 916b, 916b' so that once fully inserted, the buccal tube and connector are locked between protrusion 936" and head 940". The leading edge of locking protrusion 936" may be tapered as shown to facilitate easier insertion of the split distal end of pin 934" into the channel 916, 916'. Other suitable coupling pin configurations will be apparent to those of skill in the art in light of the present disclosure.

Figure 21:
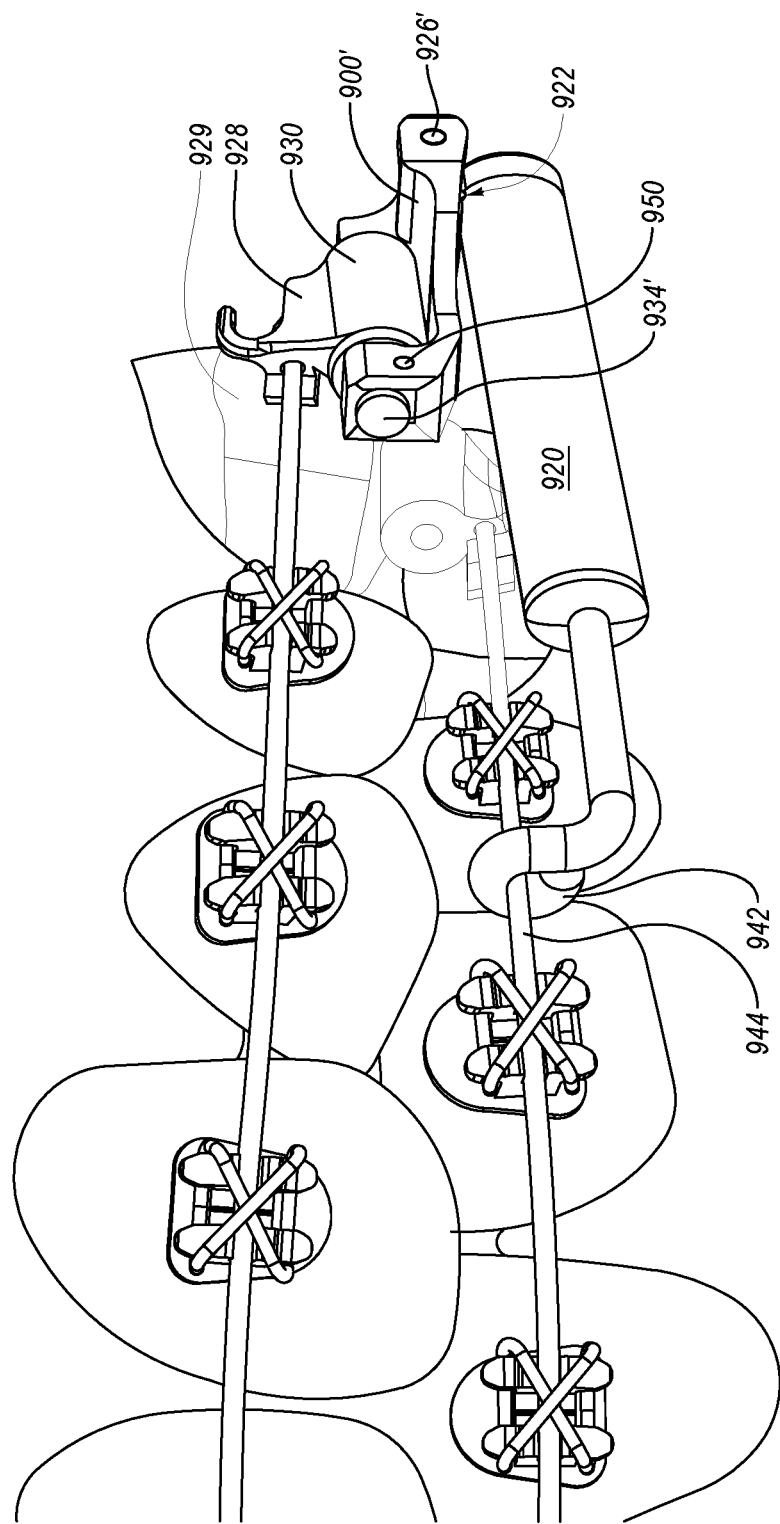
FIG. 21 is a perspective view of the connector assembly of FIG. 18 installed so as to indirectly couple a flange near a distal end of the force module to the buccal tube of the molar bracket secured to the patient's molar.

FIG. 21 is a perspective view of connector body 900' installed within a patient's mouth and coupled between buccal tube 930 of molar bracket 928 (which is secured to the patient's upper molar by band 929) and flange 922 of force module 920. The coupling is dynamic in that it allows the patient to open and close his or her mouth while the various components involved within the coupling (e.g., buccal tube 930, connector body 900', flange 922) are allowed to adjust by rotation about pin hinges 934' and 926' as necessitated by the patient's jaw movements. The proximal end of force module 920 is coupled to the arch wire 944 of the lower dental arch through hook 942. Although hook 942 is illustrated as coupled to lower arch wire 944, it will be understood that any suitable coupling mechanism may be used for coupling the proximal end of the force module 920 to the lower arch wire or bracket of the lower dental arch. Stop 948 (see FIG. 17) prevents connector 900' and coupled force module 920 from excessively rotating outwardly away from the patient's teeth towards the cheek. It will also be understood that orthodontic force modules other than those described herein may be connected to a buccal tube bracket by any of the above described connectors and connector assemblies.

VI. Exemplary Materials Used to Manufacture an Orthodontic Force Module or Assembly and Latch Mechanism The orthodontic force modules and assemblies of the present invention may be formed from any suitable material(s), such as one or more metals or allows and/or polymers. According to one embodiment, at least the outer body, plunger and push rod can be made from stainless steel (e.g., 316L) or other biocompatible metal or alloy. According to another embodiment, at least some of the components of the orthodontic force modules and assemblies may include a molded polymer material.

To prevent fatigue and provide a spring that provides more reliable spring-back action and consistent corrective forces over time, the spring may comprise a Co—Cr—Ni alloy, such as Elgiloy®. According to one embodiment, the spring comprises a compressible coil spring.

The components of the orthodontic force modules and assemblies may be manufactured using any appropriate molding and/or machining process known in the art and that is suitable for the particular material being acted upon. For example, at least some of the components may be made by machining, casting, injection molding, metal injection molding (MIM), additive manufacturing processes, drawing and the like. Machining at least the elongate body may be advantageous as better accuracy of the component dimensions may be possible as compared to alternative techniques (e.g., drawing). Such improved accuracy provides for better fit as well as improved wall thickness. Miniaturization of the components, increased strength, and accurate fit are possible by machining. For example, a machined elongate body may include a wall thickness substantially greater than that of existing devices formed by drawing.

Furthermore, the overall dimensions of machined devices, particularly width, are significantly less than existing devices. This provides a device having significantly lower profile compared to existing force modules, which increases comfort and reduces contact with soft oral tissue during use. Moreover, machining can provide enhanced durability compared to devices made by metal injection molding.

As used in this specification and the appended claims, the singular forms "a," "an" and "the" include plural referents unless the context clearly dictates otherwise.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A force module for use in orthodontic correction, comprising:
   an elongate hollow body having a proximal end and a distal end;
   a proximal end cap having a proximal portion at the proximal end of the elongate hollow body, a distal extension disposed within the elongate hollow body, and a passageway extending through the proximal end cap, including through the proximal portion and the distal extension;

a plunger having an enlarged proximal end disposed within the elongate hollow body and a hollow passageway extending through the plunger and the enlarged proximal end; and a biasing member confined between the proximal end cap and the enlarged proximal end of the plunger and positioned around at least a portion of the distal extension of the proximal end cap.

2. The force module of claim 1, further comprising a distal end cap positioned at the distal end of the elongate hollow body and having a passageway extending through the distal end cap, wherein a distal portion of the plunger extends through the passageway of the distal end cap and beyond the distal end of the elongate hollow body.

3. The force module of claim 2, wherein the passageway through the distal end cap is smaller than the enlarged proximal end of the plunger so as to confine the enlarged proximal end of the plunger within the elongate hollow body.

4. The force module of claim 1, wherein the biasing member comprises a compressible spring that bears against the enlarged proximal end of the plunger to urge the plunger distally relative to the hollow body.

5. The force module of claim 1, further comprising a push rod positionable in the passageway through the proximal end cap.

6. The force module of claim 5, wherein the push rod is configured to not engage the biasing member.

7. The force module of claim 5, wherein the push rod further includes a detent that limits distal movement of the push rod relative to the elongate hollow body.

8. The force module of claim 7, wherein the detent is larger than the passageway through proximal end cap.

9. The force module of claim 5, wherein the push rod includes a distal portion that is positionable in the passageway through the plunger.

10. The force module of claim 5, further comprising a proximal attachment member at a proximal end of the push rod for attachment to a bracket and/or an arch wire.

11. The force module of 10, wherein the proximal attachment member comprises a hook or flange.

12. The force module of claim 1, further comprising a distal attachment member at a distal end of the plunger for attachment to a bracket and/or an arch wire.

13. The force module of claim 12, wherein the distal attachment member means comprises a flange and/or a bendable wire.

14. The force module of claim 12, wherein the distal attachment member means comprises a pin member and a latch member.

15. The force module of claim 1, wherein the hollow body has a substantially circular cross section.

16. A force module for use in orthodontic correction, comprising:
an elongate hollow body having a proximal end and a distal end;

a proximal end cap having a proximal portion positioned at the proximal end of the elongate hollow body, a distal extension disposed within the elongate hollow body, and a passageway extending through the proximal end cap, including through the proximal portion and the distal extension;

a distal end cap at the distal end of the elongate hollow body and having a passageway extending through the distal end cap;

a plunger having an enlarged proximal end disposed within the elongate hollow body, a hollow passageway extending through the plunger and the enlarged proximal end, and a distal portion passing through the passageway of through the distal end cap; and a biasing member confined between the proximal end cap and the enlarged proximal end of the plunger and positioned around at least a portion of the distal extension of the proximal end cap.

17. The force module of claim 16, further comprising a push rod positionable in the passageway through the proximal end cap.

18. The force module of claim 17, wherein the push rod further includes a detent that is larger than the passageway through the proximal end cap so as to limit distal movement of the push rod when abutting the proximal end cap.

19. A force module for use in orthodontic correction, comprising:
an elongate hollow body having a proximal end and a distal end;

a proximal end cap having a proximal portion positioned at the proximal end of the elongate hollow body, a distal extension disposed within the elongate hollow body, and a passageway extending through the proximal end cap, including through the proximal portion and the distal extension;

a plunger having an enlarged proximal end disposed within the elongate hollow body and a hollow passageway extending through the plunger and the enlarged proximal end;

a biasing member confined between the proximal end cap and the enlarged proximal end of the plunger and having a passageway therethrough, wherein the biasing member is positioned around at least a portion of the distal extension of the proximal end cap; and a push rod with a distal end portion positionable in the passageway of through the proximal end cap, the passageway through the biasing member, and the hollow passageway through the plunger.

20. The force module of claim 19, further comprising a distal end cap positioned at the distal end of the elongate hollow body and having a passageway extending therethrough, a distal portion of the plunger extending through the passageway of the distal end cap and beyond the distal end of the elongate hollow body, and wherein the passageway of the distal end cap is smaller than the enlarged proximal end of the plunger so as to confine the enlarged proximal end of the plunger within the elongate hollow body.

* * * * *

UNITED STATES PATENT AND TRADEMARK OFFICE
CERTIFICATE OF CORRECTION

Page 1 of 2

PATENT NO. : 10,568,718 B2
APPLICATION NO. : 15/808163
DATED : February 25, 2020
INVENTOR(S) : Radmall et al.

It is certified that error appears in the above-identified patent and that said Letters Patent is hereby corrected as shown below:

In the Specification

Column 3
Line 35, change "comprises" to –comprise–

Column 9
Line 42, change "to substantially" to –to be substantially–

Column 10
Line 5, change "used" to –use–
Line 59, change first instance of "to" to –so–

Column 14
Line 10, remove [are]
Line 59, change "latch mechanism" to –the latch mechanism–

Column 15
Line 25, change "progressively" to –are progressively–

Column 16
Line 6, change "to" to –a–

Column 19
Line 25, change "in" to –an–

Column 24
Line 13, change "allows" to –alloys–
Line 43, change "having significantly" to –having a significantly–

Signed and Sealed this
Seventh Day of July, 2020

Andrei Iancu
*Director of the United States Patent and Trademark Office*

In the Claims

Column 26
Line 14, delete "of"